United States Patent
Yamada

(10) Patent No.: US 12,230,125 B2
(45) Date of Patent: Feb. 18, 2025

(54) SUCTION DEVICE, INFORMATION TRANSMISSION METHOD, AND NON-TRANSITORY COMPUTER READABLE MEDIUM

(71) Applicant: JAPAN TOBACCO INC., Tokyo (JP)

(72) Inventor: Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 107 days.

(21) Appl. No.: 17/988,389

(22) Filed: Nov. 16, 2022

(65) Prior Publication Data

US 2023/0083064 A1 Mar. 16, 2023

Related U.S. Application Data

(63) Continuation of application No. PCT/JP2020/041794, filed on Nov. 10, 2020.

(51) Int. Cl.
*G08C 17/02* (2006.01)
*A24F 40/57* (2020.01)
(Continued)

(52) U.S. Cl.
CPC ............ *G08C 17/02* (2013.01); *A24F 40/57* (2020.01); *A61M 11/042* (2014.02); *A24F 40/10* (2020.01);
(Continued)

(58) Field of Classification Search
CPC ............... G08C 17/02; A61M 11/042; A61M 2205/3327; A61M 2205/3368; A61M 2205/3569; A61M 2205/3653; A61M 2230/43; A24F 40/57; A24F 40/10; H04B 5/70
(Continued)

(56) References Cited

U.S. PATENT DOCUMENTS

| 10,653,187 | B1 * | 5/2020 | Doyle | A24F 40/50 |
| 2014/0261414 | A1 * | 9/2014 | Weitzel | A61M 15/0051 128/203.14 |

(Continued)

FOREIGN PATENT DOCUMENTS

| JP | 2019-521739 A | 8/2019 |
| JP | 2020-513241 A | 5/2020 |

(Continued)

OTHER PUBLICATIONS

International Search Report, issued in PCT/JP2020/041794, PCT/ISA/210, dated Jan. 26, 2021.
(Continued)

*Primary Examiner* — Zhen Y Wu
(74) *Attorney, Agent, or Firm* — Birch, Stewart, Kolasch & Birch, LLP

(57) ABSTRACT

A suction device includes a heating unit that heats a base material and generates an aerosol; a communication unit that receives, through a communication link, information indicating a profile stipulating an operation of the heating unit; and a control unit that controls the operation of the heating unit in accordance with the information indicating the profile. The information indicating the profile includes a combination of information indicating time and information indicating a parameter pertaining to the operation of the heating unit at said time.

19 Claims, 13 Drawing Sheets

(51) Int. Cl.
  *A61M 11/04*   (2006.01)
  *A24F 40/10*   (2020.01)
  *H04B 5/70*    (2024.01)
(52) U.S. Cl.
  CPC .............. *A61M 2205/3327* (2013.01); *A61M 2205/3368* (2013.01); *A61M 2205/3569* (2013.01); *A61M 2205/3653* (2013.01); *A61M 2230/43* (2013.01); *H04B 5/70* (2024.01)
(58) Field of Classification Search
  USPC .................................................. 340/539.12
  See application file for complete search history.

(56) References Cited

U.S. PATENT DOCUMENTS

| | | | | |
|---|---|---|---|---|
| 2014/0345633 A1* | 11/2014 | Talon | ...................... | A24F 40/53 702/30 |
| 2016/0331036 A1* | 11/2016 | Cameron | ................. | H04Q 9/00 |
| 2018/0043114 A1* | 2/2018 | Bowen | .................... | A24F 40/65 |
| 2020/0305512 A1* | 10/2020 | Lim | .................... | H05B 1/0297 |
| 2021/0023316 A1* | 1/2021 | Schorr | .................... | G16H 50/70 |
| 2021/0068454 A1* | 3/2021 | Jung | ........................ | A24F 40/46 |
| 2021/0161210 A1* | 6/2021 | Lee | ......................... | G06F 21/31 |
| 2021/0195959 A1* | 7/2021 | Lee | ......................... | A24F 40/51 |
| 2022/0096760 A1* | 3/2022 | Schwartz | ........... | A61M 15/0003 |

FOREIGN PATENT DOCUMENTS

| | | |
|---|---|---|
| WO | WO 2017/205692 A1 | 11/2017 |
| WO | WO 2018/098371 A1 | 5/2018 |
| WO | WO 2019/104227 A1 | 5/2019 |

OTHER PUBLICATIONS

Extended European Search Report for European Application No. 20961481.7, dated Sep. 20, 2024.

* cited by examiner

FIG. 12

| ROW | COLUMN °C\s | a 20s | b 40s | c 60s | ... | l 240s | m 260s | o 280s | p 300s | r 320s | ... |
|---|---|---|---|---|---|---|---|---|---|---|---|
| 1 | 200°C | 0 | 0 | 0 | ... | 0 | 0 | 0 | 0 | 0 | ... |
| 2 | 210°C | 0 | 0 | 0 | ... | 0 | 0 | 0 | 0 | 0 | ... |
| 3 | 220°C | 0 | 0 | 1 | ... | 0 | 0 | 0 | 1 | 0 | ... |
| 4 | 230°C | 0 | 0 | 0 | ... | 1 | 1 | 0 | 0 | 0 | ... |
| 5 | 240°C | 0 | 0 | 0 | ... | 0 | 0 | 0 | 0 | 0 | ... |
| 6 | 250°C | 1 | 0 | 0 | ... | 0 | 0 | 0 | 0 | 0 | ... |
| ⋮ | ⋮ | ⋮ | ⋮ | ⋮ | ⋮ | ⋮ | ⋮ | ⋮ | ⋮ | ⋮ | ⋮ |
| 10 | 290°C | 0 | 0 | 0 | ... | 0 | 0 | 0 | 0 | 0 | ... |
| 11 | 300°C | 0 | 0 | 0 | ... | 0 | 0 | 0 | 0 | 0 | ... |
| ⋮ | ⋮ | ⋮ | ⋮ | ⋮ | ⋮ | ⋮ | ⋮ | ⋮ | ⋮ | ⋮ | ⋮ |

FIG. 14

| | COLUMN | a | b | c | ... | l | m | o | p | r | ... |
|---|---|---|---|---|---|---|---|---|---|---|---|
| ROW | Ω \ s | 20s | 40s | 60s | ... | 240s | 260s | 280s | 300s | 320s | ... |
| 1 | 1.00 Ω | 0 | 0 | 0 | ... | 0 | 0 | 0 | 0 | 0 | ... |
| 2 | 1.10 Ω | 0 | 0 | 0 | ... | 0 | 0 | 0 | 0 | 0 | ... |
| 3 | 1.20 Ω | 0 | 0 | 1 | ... | 0 | 0 | 0 | 1 | 0 | ... |
| 4 | 1.30 Ω | 0 | 0 | 0 | ... | 1 | 1 | 0 | 0 | 0 | ... |
| 5 | 1.40 Ω | 0 | 0 | 0 | ... | 0 | 0 | 0 | 0 | 0 | ... |
| 6 | 1.50 Ω | 1 | 0 | 0 | ... | 0 | 0 | 0 | 0 | 0 | ... |
| ⋮ | ⋮ | ⋮ | ⋮ | ⋮ | ⋮ | ⋮ | ⋮ | ⋮ | ⋮ | ⋮ | ⋮ |
| 10 | 1.90 Ω | 0 | 0 | 0 | ... | 0 | 0 | 0 | 0 | 0 | ... |
| 11 | 2.00 Ω | 0 | 0 | 0 | ... | 0 | 0 | 0 | 0 | 0 | ... |
| ⋮ | ⋮ | ⋮ | ⋮ | ⋮ | ⋮ | ⋮ | ⋮ | ⋮ | ⋮ | ⋮ | ⋮ |

SUCTION DEVICE, INFORMATION TRANSMISSION METHOD, AND NON-TRANSITORY COMPUTER READABLE MEDIUM

TECHNICAL FIELD

The present invention relates to an inhaler device, an information transmission method, and a non-transitory computer readable medium. This application is a continuation application based on International Patent Application No. PCT/JP2020/041794 filed on Nov. 10, 2020, and the content of the PCT international application is incorporated herein by reference.

BACKGROUND ART

Inhaler devices that generate material to be inhaled by a user, such as electronic cigarettes and nebulizers, have been widely used. For example, by using a substrate that contains an aerosol source for generating an aerosol and a flavor source for imparting a flavor component to the generated aerosol, an inhaler device generates an aerosol having a flavor component imparted thereto. The user can enjoy a flavor by inhaling an aerosol having a flavor component imparted thereto generated by the inhaler device.

In recent years, an addition of wireless communication capabilities to inhaler devices has been examined. For example, Patent Literature 1 discloses a technique that enables an inhaler device to operate in accordance with operation settings wirelessly received from a mobile communication device.

CITATION LIST

Patent Literature

Patent Literature 1: International Publication No. 2019/104227

SUMMARY OF INVENTION

Technical Problem

However, the technique described in Patent Literature 1 has not necessarily been designed well enough in terms of the volume of communication of the inhaler device.

The present invention has been made to address the problem described above. An object of the present invention is to provide a mechanism that can reduce the volume of communication of an inhaler device.

Solution to Problem

To solve the problem described above, an aspect of the present invention provides an inhaler device that includes a heater configured to heat a substrate to generate an aerosol; a communicator configured to receive, through a communication link, information indicating a profile defining an operation of the heater; and a controller configured to control the operation of the heater in accordance with the information representing the profile. The information representing the profile includes a combination of information representing time and information representing a parameter related to the operation of the heater at the time.

The profile may be information that represents temporal changes in parameter related to the operation of the heater in a period from a start time point to an end time point. The information representing the time may be information that represents each of a plurality of time segments constituting the period from the start time point to the end time point.

The information representing the time segment may be information that represents a sequential position of the time segment and a length of the time segment.

The information representing the time segment may be information that represents an end of the time segment as a period of time elapsed from the start time point.

The information representing the time segment may be information that represents each of a beginning and an end of the time segment as a period of time elapsed from the start time point.

The information representing the parameter related to the operation of the heater may be information that represents a target value to be reached by the parameter at the time.

The information representing the profile may be information that represents temporal changes in parameter related to the operation of the heater in a period from a start time point to an end time point. The information representing the parameter related to the operation of the heater may be information that represents temporal change in parameter at the time.

The information that represents temporal change in parameter may be information that represents a function approximating a shape of the temporal change in parameter at the time.

The profile may be information that represents temporal changes in parameter related to the operation of the heater in a period from a start time point to an end time point. The information representing the time may be information that represents each of a plurality of time segments constituting the period from the start time point to the end time point. The information representing the parameter related to the operation of the heater may be information that represents temporal change in parameter in the time segment. The communicator may receive, through the communication link, information that includes, for each of the plurality of time segments constituting the period from the start time point to the end time point, a combination of information representing the time segment and information representing temporal change in parameter in the time segment.

As the information representing the profile, the communicator may transmit information from which information representing a target value of the parameter related to the operation of the heater in at least part of the time is omitted.

If the information representing the profile received does not include information representing a target value of the parameter related to the operation of the heater in a first time period, the controller may use information representing a target value of the parameter related to the operation of the heater in a second time period as the information representing the target value of the parameter related to the operation of the heater in the first time period. The second time period is one time period before the first time period.

The parameter may be information detected when the heater operates.

The parameter may be a temperature of the heater, or a resistance of the heater.

The parameter may be a temperature of a region heated by the heater.

The parameter may relate to electricity supplied to the heater.

The parameter may be the amount of the aerosol inhaled by a user. The aerosol is generated by the heater.

The communication link may be wireless.

The communicator may transmit the information representing the profile through NFC.

To solve the problem described above, another aspect of the present invention provides an information transmission method that includes transmitting through a communication link, as information representing a profile defining an operation of a heater configured to heat a substrate to generate an aerosol, a combination of information representing time and information representing a parameter related to the operation of the heater at the time.

To solve the problem described above, another aspect of the present invention provides a non-transitory computer readable medium having a program stored therein, the program that causes a computer to control an inhaler device that controls an operation of a heater configured to heat a substrate to generate an aerosol. The program causes the computer to control the inhaler device in such a way that through a communication link, the inhaler device transmits, as information representing a profile defining the operation of the heater for heating the substrate to generate an aerosol, a combination of information representing time and information representing a parameter related to the operation of the heater at the time.

ADVANTAGEOUS EFFECTS OF INVENTION

As described above, the present invention provides a mechanism that can reduce the volume of communication of the inhaler device.

BRIEF DESCRIPTION OF DRAWINGS

FIG. 12 is a diagram illustrating an example of a common table that defines target temperatures according to the second modification example.

FIG. 14 is a diagram illustrating an example of a common table that defines target resistances according to the second modification example.

DESCRIPTION OF EMBODIMENTS

Figure 1:
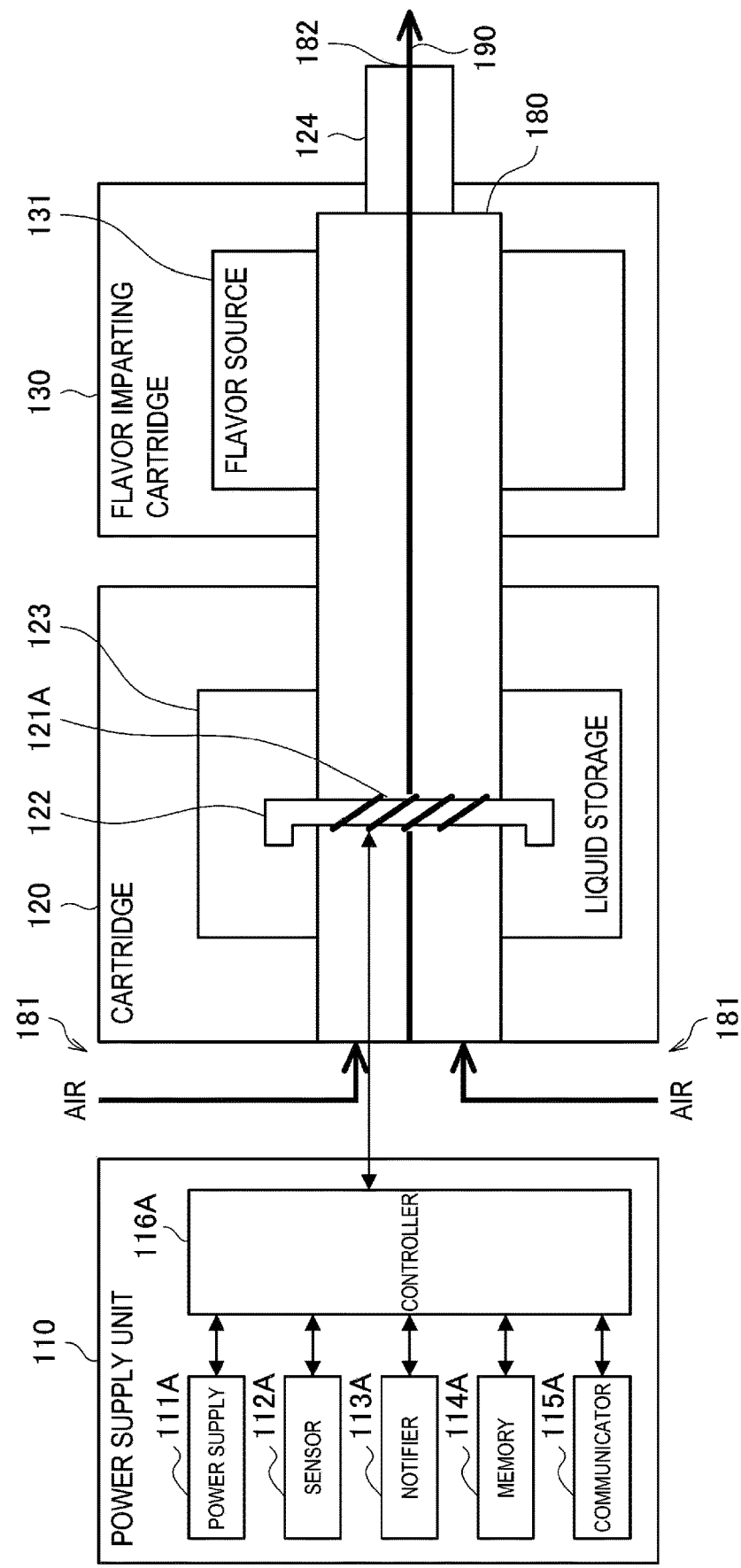
FIG. 1 is a schematic diagram of an inhaler device according to a first configuration example.

Preferred embodiments of the present invention will now be described in detail with reference to the accompanying drawings. In the present specification and drawings, overlapping description of structural elements having substantially the same functions and configurations will be omitted by assigning the same reference numerals.

1. Configuration Example of Inhaler Device

An inhaler device generates material to be inhaled by a user. In the example described below, the material generated by the inhaler device is an aerosol. Alternatively, the material generated by the inhaler device may be gas.

(1) First Configuration Example

FIG. 1 is a schematic diagram of the inhaler device according to the first configuration example. As illustrated in FIG. 1, an inhaler device 100A according to the present configuration example includes a power supply unit 110, a cartridge 120, and a flavor imparting cartridge 130. The power supply unit 110 includes a power supply 111A, a sensor 112A, a notifier 113A, a memory 114A, a communicator 115A, and a controller 116A. The cartridge 120 includes a heater 121A, a liquid guide 122, and a liquid storage 123. The flavor imparting cartridge 130 includes a flavor source 131 and a mouthpiece 124. In the cartridge 120 and the flavor imparting cartridge 130, an airflow path 180 is defined.

The power supply 111A stores electric power. The power supply 111A supplies electric power to the structural elements of the inhaler device 100A under the control of the controller 116A. The power supply 111A may be a rechargeable battery such as a lithium ion secondary battery.

The sensor 112A acquires various items of information regarding the inhaler device 100A. In an example, the sensor 112A may be a pressure sensor such as a microphone condenser, a flow sensor, or a temperature sensor, and acquire a value generated in accordance with the user's inhalation. In another example, the sensor 112A may be an input device that receives information input by the user, such as a button or a switch.

The notifier 113A provides information to the user. The notifier 113A may be a light-emitting device that emits light, a display device that displays an image, a sound output device that outputs sound, or a vibration device that vibrates.

The memory 114A stores various items of information for operation of the inhaler device 100A. The memory 114A may be a non-volatile storage medium such as flash memory.

The communicator 115A is a communication interface capable of communication in conformity with any wired or wireless communication standard. Such a communication standard may be, for example, Wi-Fi (registered trademark) or Bluetooth (registered trademark).

The controller 116A functions as an arithmetic processing unit and a control circuit, and controls the overall operations of the inhaler device 100A in accordance with various programs. The controller 116A includes electronic circuits such as a central processing unit (CPU) and a microprocessor, for example.

The liquid storage 123 stores an aerosol source. The aerosol source is atomized to generate an aerosol. The aerosol source includes liquids such as polyhydric alcohol and water. Examples of the polyhydric alcohol include glycerine and propylene glycol. The aerosol source may include a flavor component that is either derived from tobacco or not derived from tobacco. For the inhaler device 100A that is a medical inhaler such as a nebulizer, the aerosol source may include a medicine.

The liquid guide 122 guides, from the liquid storage 123, the aerosol source that is the liquid stored in the liquid storage 123, and holds the aerosol source. The liquid guide 122 is, for example, a wick formed by twining fiber material such as glass fiber or porous material such as porous ceramic. In this case, the capillary action of the wick guides the aerosol source stored in the liquid storage 123.

The heater 121A heats the aerosol source to atomize the aerosol source and generate the aerosol. In the example illustrated in FIG. 1, the heater 121A includes a coil wound around the liquid guide 122. When the heater 121A produces heat, the aerosol source held by the liquid guide 122 is heated and atomized to generate the aerosol. The heater 121A produces heat when receiving electric power from the power supply 111A. In an example, the electric power may be supplied in response to the sensor 112A detecting a start of the user's inhalation and/or an input of predetermined information. Subsequently, the supply of the electric power may be stopped in response to the sensor 112A detecting an end of the user's inhalation and/or an input of predetermined information.

The flavor source 131 is a structural element for imparting a flavor component to the aerosol. The flavor source 131 may include a flavor component that is either derived from tobacco or not derived from tobacco.

The airflow path 180 is a flow path of air to be inhaled by the user. The airflow path 180 has a tubular structure having an air inlet hole 181 and an air outlet hole 182 at both ends. The air inlet hole 181 is an inlet of air into the airflow path 180, and the air outlet hole 182 is an outlet of the air from the airflow path 180. The liquid guide 122 is on the airflow path 180 at an upstream position (closer to the air inlet hole 181), and the flavor source 131 is on the airflow path 180 at a downstream position (closer to the air outlet hole 182). Air flowing in through the air inlet hole 181 when the user inhales mixes with the aerosol generated by the heater 121A. Subsequently, as indicated by an arrow 190, the mixture fluid of the aerosol and the air passes through the flavor source 131 and is conveyed to the air outlet hole 182. When the mixture fluid of the aerosol and the air passes through the flavor source 131, the flavor component included in the flavor source 131 is imparted to the aerosol.

The mouthpiece 124 is to be held in a mouth of the user during inhalation. The mouthpiece 124 has the air outlet hole 182. When the user inhales with the mouthpiece 124 in his/her mouth, the mixture fluid of the aerosol and the air enters the oral cavity of the user.

The configuration example of the inhaler device 100A has been described above. The inhaler device 100A is not limited to the above configuration, and may be configured in various ways as exemplified below.

In an example, the inhaler device 100A does not have to include the flavor imparting cartridge 130. In this case, the cartridge 120 includes the mouthpiece 124.

In another example, the inhaler device 100A may include various types of aerosol sources. Still another type of aerosol may be generated by mixing a plurality of types of aerosols generated from the plurality of types of aerosol sources in the airflow path 180 and causing a chemical reaction.

In addition, means for atomizing the aerosol source is not limited to heating by the heater 121A. For example, the means for atomizing the aerosol source may be vibration atomization or induction heating.

(2) Second Configuration Example

Figure 2:
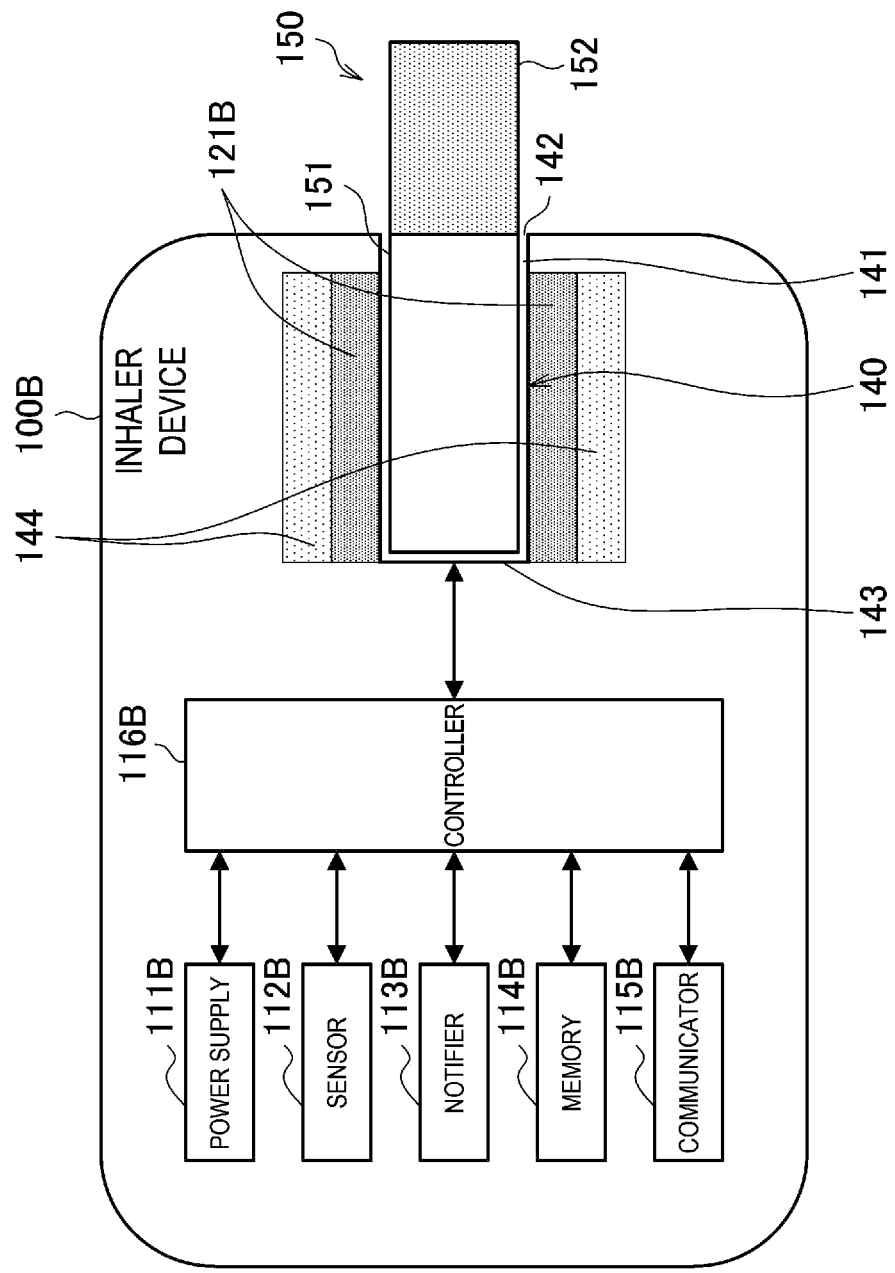
FIG. 2 is a schematic diagram of an inhaler device according to a second configuration example.

FIG. 2 is a schematic diagram of the inhaler device according to the second configuration example. As illustrated in FIG. 2, an inhaler device 100B according to the present configuration example includes a power supply 111B, a sensor 112B, a notifier 113B, a memory 114B, a communicator 115B, a controller 116B, a heater 121B, a holder 140, and a heat insulator 144.

The power supply 111B, the sensor 112B, the notifier 113B, the memory 114B, the communicator 115B, and the controller 116B are substantially the same as the respective corresponding structural elements included in the inhaler device 100A according to the first configuration example.

The holder 140 has an internal space 141, and holds a stick substrate 150 in a manner partially accommodated in the internal space 141. The holder 140 has an opening 142 that allows the internal space 141 to communicate with outside. The holder 140 accommodates the stick substrate 150 that is inserted into the internal space 141 through the opening 142. For example, the holder 140 may be a tubular body having the opening 142 and a bottom 143 on its ends, and may define the pillar-shaped internal space 141. The holder 140 also has the function of defining the flow path of air supplied to the stick substrate 150. For example, the bottom 143 has an air inlet hole that is an inlet of air into the flow path. The opening 142 is an air outlet hole that is an outlet of air from the flow path.

The stick substrate 150 includes a substrate 151 and an inhalation port 152. The substrate 151 includes an aerosol source. In the present configuration example, the aerosol source is not limited to a liquid and may be a solid. The stick substrate 150 held by the holder 140 includes the substrate 151 at least partially accommodated in the internal space 141 and the inhalation port 152 at least partially protruding from the opening 142. When the user inhales with the inhalation port 152 protruding from the opening 142 in his/her mouth, air flows into the internal space 141 through the airflow path (not illustrated), and the air and an aerosol generated from the substrate 151 reach inside the mouth of the user.

The heater 121B has the same configuration as the heater 121A according to the first configuration example. In the example illustrated in FIG. 2, however, the heater 121B has a film-like shape and surrounds the outer circumference of the holder 140. Subsequently, heat produced from the heater 121B heats the substrate 151 of the stick substrate 150 from the outer circumference, generating the aerosol.

The heat insulator 144 prevents heat from transferring from the heater 121B to the other structural elements. For example, the heat insulator 144 may be a vacuum heat insulator or an aerogel heat insulator.

The configuration example of the inhaler device 100B has been described above. The inhaler device 100B is not limited to the above configuration, and may be configured in various ways as exemplified below.

In an example, the heater 121B may have a blade-like shape, and may be disposed so that the heater 121B protrudes from the bottom 143 of the holder 140 toward the internal space 141. In this case, the heater 121B having the blade-like shape is inserted into the substrate 151 of the stick substrate 150 and heats the substrate 151 of the stick substrate 150 from its inside. In another example, the heater 121B may be disposed so that the heater 121B covers the bottom 143 of the holder 140. In still another example, the heater 121B may be implemented as a combination of two or more selected from a first heater that covers the outer circumference of the holder 140, a second heater having the blade-like shape, and a third heater that covers the bottom 143 of the holder 140.

In another example, the holder 140 may include an opening/closing mechanism that at least partially opens and closes an outer shell defining the internal space 141. Examples of the opening/closing mechanism include a hinge. In addition, the holder 140 may accommodate the stick substrate 150 while sandwiching the stick substrate 150 inserted into the internal space 141 by opening and closing the outer shell. In this case, the heater 121B may be at the sandwiching position of the holder 140 and may produce heat while pressing the stick substrate 150.

In addition, means for atomizing the aerosol source is not limited to heating by the heater 121B. For example, the means for atomizing the aerosol source may be induction heating.

In addition, the inhaler device 100B may also include the heater 121A, the liquid guide 122, the liquid storage 123, and the airflow path 180 according to the first configuration example. The air outlet hole 182 for the airflow path 180 may also serve as an air inlet hole for air into the internal space 141. In this case, a mixture fluid of the air and an aerosol generated by the heater 121A flows into the internal space 141, mixes further with an aerosol generated by the heater 121B, and then reaches the oral cavity of the user.

Supplemental Remarks

The inhaler device 100 may have any configuration example, either the first configuration example or the second configuration example, described above. In the following description, a user's inhalation of an aerosol generated by the inhaler device 100 may simply be referred to as "inhalation" or "puff".

The inhaler device 100 according to the present embodiment uses a substrate to generate an aerosol to be inhaled by the user. The heater 121 is an example of a generator that generates an aerosol. The cartridge 120 and the flavor imparting cartridge 130 according to the first configuration example, and the stick substrate 150 according to the second configuration example, are examples of the substrate according to the present invention. The inhaler device 100 generates an aerosol by using a substrate mounted in the inhaler device 100. In the first configuration example, the cartridge 120 and the flavor imparting cartridge 130 connected to the power supply unit 110 are examples of the substrate mounted in the inhaler device 100. In the second configuration example, the stick substrate 150 inserted in the inhaler device 100 is an example of the substrate mounted in the inhaler device 100.

2. Technical Features (1) Heating Profile

The inhaler device 100 according to the present embodiment operates in accordance with a heating profile. The heating profile is information that defines an operation performed by the inhaler device 100 to generate an aerosol (i.e., operation performed by the heater 121 to heat a substrate). The controller 116 performs control to cause the heater 121 to operate in accordance with a heating profile, so that an aerosol is generated.

The heating profile is information that represents temporal changes in parameter related to the operation of the heater 121 in a period from a start time point to an end time point. In particular, the heating profile may be information that represents temporal changes of a target value of the parameter related to the operation of the heater 121. In this case, the inhaler device 100 controls the operation of the heater 121 in such a way that the parameter related to the operation of the heater 121 changes in accordance with the temporal changes of the target value defined by the heating profile.

An example of the parameter is the temperature of the heater 121. Hereinafter, the target value of the temperature of the heater 121 in the heating profile is also referred to as a target temperature. The controller 116 controls the temperature of the heater 121 in such a way that the same temperature as the target temperature defined by the heating profile is attained by the heater 121. The temperature control in the heater 121 can be performed, for example, by known feedback control. Specifically, the controller 116 causes electric power from the power supply 111 to be supplied to the heater 121 in a pulse-width modulation (PWM) mode or pulse-frequency modulation (PFM) mode. In this case, the controller 116 adjusts the duty ratio of power pulses to perform the temperature control in the heater 121.

The feedback control requires the controller 116 to simply control the electric power supplied to the heater 121, or for example the duty ratio described above, on the basis of a difference between the temperature of the heater 121 and the target temperature, for example. The feedback control may be, for example, proportional-integral-differential controller (PID controller). The temperature of the heater 121 can be quantified, for example, by measuring or estimating the electrical resistance of the heater 121 (or more precisely, a heating resistor included in the heater 121). This is because the electrical resistance of the heating resistor changes with temperature. The electrical resistance of the heating resistor can be estimated, for example, by measuring the amount of voltage drop in the heating resistor. The amount of voltage drop in the heating resistor can be measured by a voltage sensor that measures a potential difference applied to the heating resistor. In another example, the temperature of the heater 121 can be measured by a temperature sensor installed near the heater 121.

As described above, when the electrical resistance of the heater 121 changes with the temperature of the heater 121, the temperature of the heater 121 can be considered synonymous with the resistance of the heater 121. Accordingly, the target temperature of the heater 121 can also be expressed as the electrical resistance of the heater 121. In this case, an example of the parameter in the heating profile may be the resistance of the heater 121. Hereinafter, the target value of the resistance of the heater 121 in the heating profile is also referred to as a target resistance. The controller 116 may control the resistance of the heater 121 in such a way that the same resistance as the target resistance defined by the heating profile is attained by the heater 121. The resistance control in the heater 121 can be performed, for example, by known feedback control. Specifically, the controller 116 causes electric power from the power supply 111 to be supplied to the heater 121 in a pulse-width modulation (PWM) mode or pulse-frequency modulation (PFM) mode. In this case, the controller 116 adjusts the duty ratio of power pulses to perform the resistance control in the heater 121.

Although the temperature of the heater 121 has a correspondence relation with the electrical resistance of the heater 121, the resistance corresponding to the temperature of the heater 121 depends on the characteristics and ambient temperature of the heater 121. This means that even the value of the target resistance corresponding to the same target temperature varies depending on the characteristics or ambient temperature of the heater 121.

The feedback control requires the controller 116 to simply control the electric power supplied to the heater 121, or for example the duty ratio described above, on the basis of a difference between the resistance of the heater 121 and the target resistance, for example. The feedback control may be, for example, PID control. The electrical resistance of the heating resistor can be estimated, for example, by measuring the amount of voltage drop in the heating resistor.

In the first configuration example, heating by the heater 121A takes place at the time of detection of a puff. That is, the heater 121A performs heating every time a puff is detected. After the substrate is mounted in the inhaler device 100A according to the first configuration example, the aerosol source included in the substrate decreases at every puff and becomes eventually depleted. Typically, the user replaces the substrate at the time of depletion of the aerosol source.

In the second configuration example, on the other hand, heating by the heater 121B starts at the time of detection of an instruction to start heating. During heating by the heater 121B, an aerosol is generated from the substrate. After the start of heating, the aerosol source included in the substrate decreases with time. At the time of depletion of the aerosol source, the heating by the heater 121B is stopped. Typically, the user takes a puff during heating by the heater 121B.

A period in which sufficient aerosol is assumed to be generated is also referred to as a puffing period. A period from the start of heating to the start of the puffing period is also referred to as a preheating period. Heating performed during the preheating period is also referred to as preheating. The user may be notified of the time of starting and ending of the puffing period. In this case, the user can take a puff during the puffing period with reference to this notification.

There are various possible examples of the start time point and the end time point of the heating profile.

An example of the start time point of the heating profile according to the first configuration example is the time of mounting of a new substrate. An example of the end time point of the heating profile according to the first configuration example is the time of removal of a mounted substrate.

An example of the start time point of the heating profile according to the second configuration example is the time of starting of heating (or more precisely, preheating). An example of the end time point of the heating profile according to the second configuration example is the time of ending of heating by the heater 121 (or more precisely, the time of ending of the puffing period). Heating may be temporarily stopped during the period from the start to the end of the heating.

Figure 3:
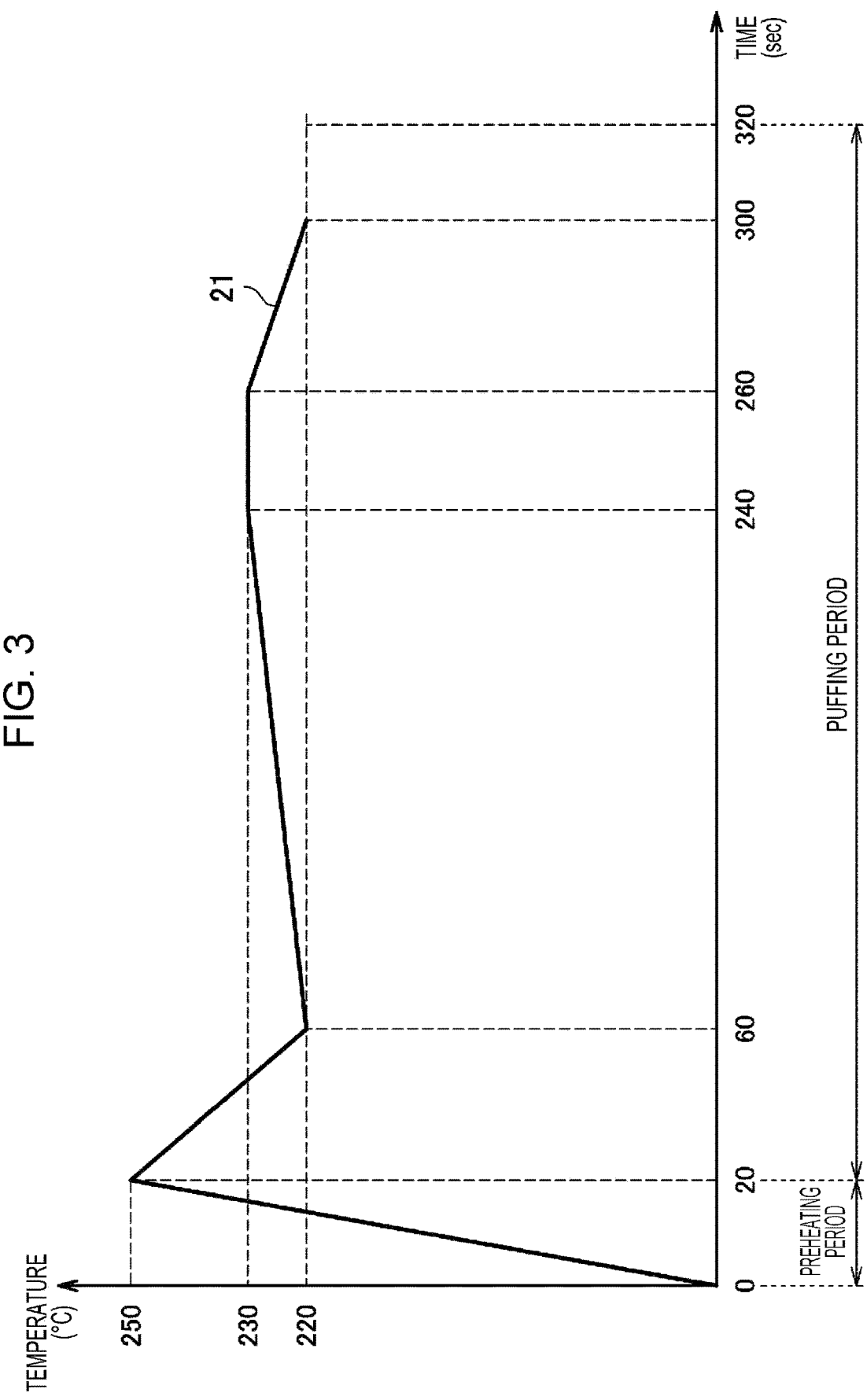
FIG. 3 is a graph showing an example of a heating profile that defines temporal changes of a target temperature according to the present embodiment.

An example of the heating profile according to the second configuration example will be described with reference to FIG. 3. FIG. 3 is a graph showing an example of a heating profile that defines temporal changes of a target temperature according to the present embodiment. The horizontal axis of the present graph represents time (in seconds). The vertical axis of the present graph represents the temperature of the heater 121. A line 21 in the present graph represents temporal changes of the target temperature in the heating profile.

The line 21 in the present graph shows that the target temperature is set to reach 250° C. in 20 seconds after the heating start, reach 220° C. in 60 seconds after the heating start, reach 230° C. in 240 seconds after the heating start, remain at 230° C. until the elapse of 260 seconds after the heating start, and finally reach 220° C. in 300 seconds after the heating start. For each of the time points described above, the controller 116 controls the temperature of the heater 121 toward the set target temperature. The temperature of the heater 121 thus changes to follow the heating profile.

In the example illustrated in FIG. 3, the first 20 seconds from the heating start is the preheating period. The puffing period thus starts in 20 seconds after the heating start. Since no target temperature is set for the period after 300 seconds from the heating start, the controller 116 causes the heater 121 to stop heating. The aerosol continues to be generated, however, as long as the residual heat of the heater 121 and the substrate remains. The puffing period ends after the heating is stopped. In the example illustrated in FIG. 3, the puffing period ends in 320 seconds after the heating start.

Figure 4:
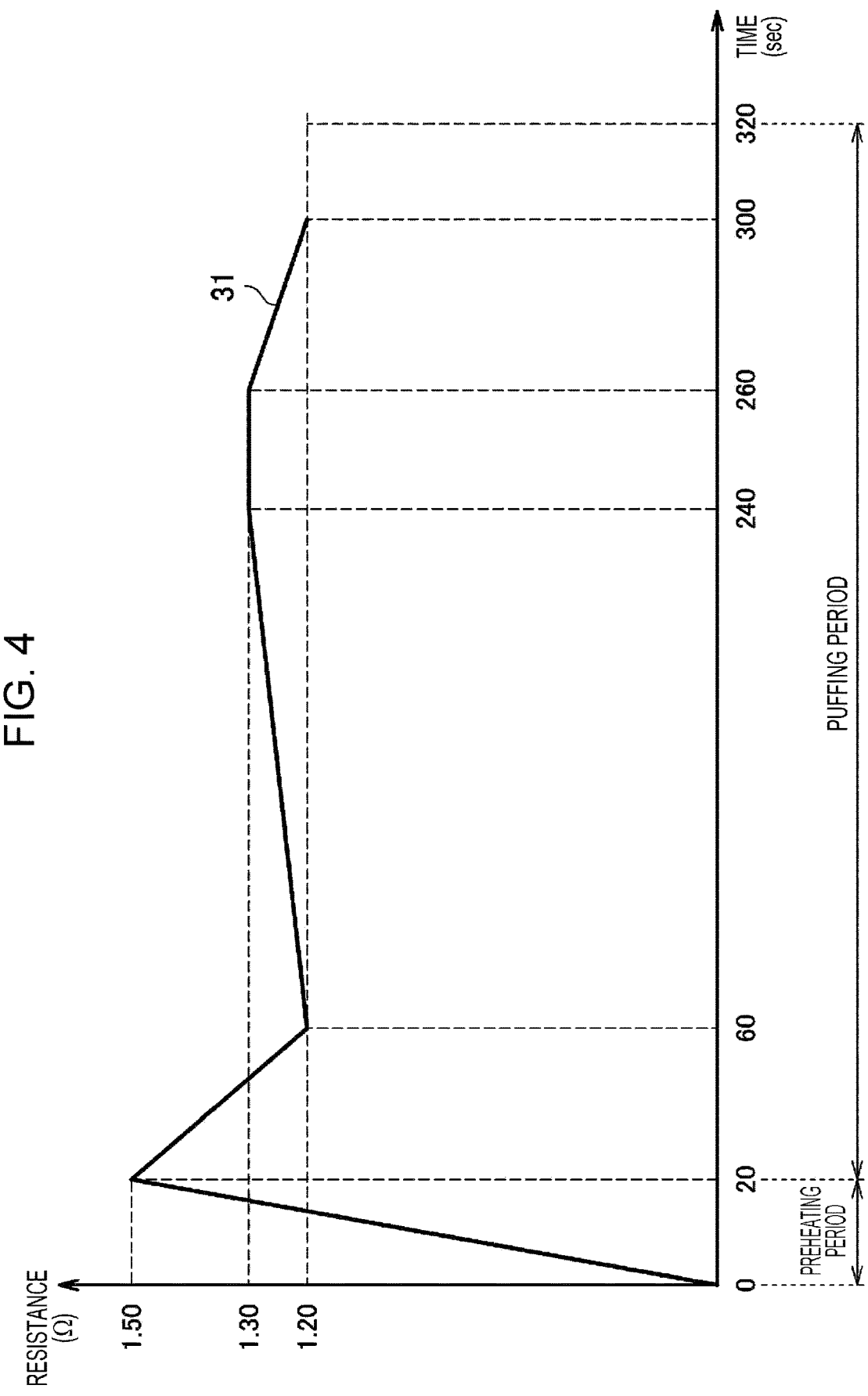
FIG. 4 is a graph showing an example of a heating profile that defines temporal changes of a target resistance according to the present embodiment.

As described above, when the electrical resistance of the heater 121 changes with the temperature of the heater 121, the heating profile may define the temporal changes of the target resistance. FIG. 4 is a graph showing an example of a heating profile that defines temporal changes of a target resistance according to the present embodiment. The horizontal axis of the present graph represents time (in seconds). The vertical axis of the present graph represents the electrical resistance (i.e., target resistance) of the heater 121, in place of the target temperature of the heater 121 represented by the vertical axis in the example illustrated in FIG. 3. A line 31 in the present graph represents temporal changes of the target resistance in the heating profile. The resistance represented by the vertical axis of the present graph is merely an example. Even the value of resistance corresponding to the same target temperature varies depending on the characteristics or ambient temperature of the heater 121.

The line 31 in the present graph shows that the target resistance is set to reach 1.50Ω in 20 seconds after the heating start, reach 1.20Ω in 60 seconds after the heating start, reach 1.30Ω in 240 seconds after the heating start, remain at 1.30Ω until the elapse of 260 seconds after the heating start, and finally reach 1.20Ω in 300 seconds after the heating start. For each of the time points described above, the controller 116 controls the resistance of the heater 121 toward the set target resistance. The resistance of the heater 121 thus changes to follow the heating profile. Since the temperature of the heater 121 changes with the electrical resistance of the heater 121, the temperature of the heater 121 is controlled on the basis of how the controller 116 controls the resistance of the heater 121.

In the example illustrated in FIG. 4, the first 20 seconds from the heating start is the preheating period. The puffing period thus starts in 20 seconds after the heating start. Since no target resistance is set for the period after 300 seconds from the heating start, the controller 116 causes the heater 121 to stop heating. The aerosol continues to be generated, however, as long as the residual heat of the heater 121 and the substrate remains. The puffing period ends after the heating is stopped. In the example illustrated in FIG. 4, the puffing period ends in 320 seconds after the heating start.

(2) Discretization of Heating Profile

The inhaler device 100 transmits and receives information representing a heating profile through a communication link. The communication link is, for example, wireless. Examples of the wireless communication standard used in this case include near-field wireless communication standards, such as near-field communication (NFC) and Bluetooth. With this configuration, the inhaler device 100 can transmit and receive information that represents a heating profile, to and from another device at a short distance. The communication link may be wired.

In an example, the inhaler device 100 transmits and receives information representing a heating profile to and from another inhaler device 100. This configuration enables the receiving side to operate in accordance with the received heating profile.

In another example, the inhaler device 100 transmits and receives information representing a heating profile to and from a terminal device, such as a smartphone. With this configuration, the terminal device can output the heating profile received from the inhaler device 100 to the user, and can customize the received heating profile on the basis of the use's operation. This can also allow the inhaler device 100 to operate in accordance with the customized heating profile received from the terminal device.

If the heating profile described above is transmitted and received as continuous data that represents temporal changes of the target temperature (or target resistance), the volume of communication increases in proportion to temporal granularity. Accordingly, in the present embodiment, the heating profile is discretized and transmitted and received as discrete data, so as to reduce the volume of communication. The details will now be described.

As information representing the heating profile, the inhaler device 100 transmits, through a communication link, information that includes a combination of information representing time and information representing a parameter at the time. More specifically, as information representing the heating profile, the inhaler device 100 wirelessly transmits information that includes, for each of a plurality of time segments (hereinafter also referred to as time sub-segments) constituting a period from a start time point to an end time point, a combination of information representing the time sub-segment and information representing temporal change in parameter in the time sub-segment. For example, the inhaler device 100 wirelessly transmits information that includes, for each of a plurality of time sub-segments into which the entire time segment (from the start to end of heating) is divided, a combination of information representing the time sub-segment and information representing temporal change of a target temperature (or target resistance) in the time sub-segment. With this configuration, the heating profile represented by continuous data is discretized into pieces of information for respective time sub-segments, each represented by discrete data. This can reduce the volume of communication in transmitting and receiving the heating profile.

A receiving side that receives information representing the heating profile represented by discrete data, can restore the heating profile represented by continuous data, on the basis of the received information. That is, in the present embodiment, the volume of communication can be reduced by so-called lossless compression of the heating profile, without substantial loss of information.

An example of a method for transmitting information that represents a heating profile will now be described. A device, such as a terminal device, which is not the inhaler device 100, may discretize and transmit the heating profile using a transmission method described below.

First Transmission Method

In a first transmission method, information representing a time sub-segment is information that represents the sequential position of the time sub-segment and information that represents the length of the time sub-segment. Also, information representing temporal change in parameter in the time sub-segment is information that represents a target value to be reached by the parameter in the time sub-segment. That is, the inhaler device 100 transmits information that includes, for each of a plurality of time sub-segments, a combination of information representing the sequential position of the time sub-segment and the length of the time sub-segment and information representing a target value to be reached by a parameter in the time sub-segment. A device, such as a terminal device, which is not the inhaler device 100, may transmit the information to the inhaler device 100.

In an example, the information representing the target value to be reached by the parameter in the time sub-segment may represent the target value to be reached by the parameter at the end of the time sub-segment. In another example, the information representing the target value to be reached by the parameter in the time sub-segment may represent the target value to be reached by the parameter at any time in the time sub-segment.

Table 1 below shows an example of information representing the heating profile in FIG. 3 and transmitted by the first transmission method.

TABLE 1

Example of information representing heating profile transmitted by first transmission method

| Information of Time Sub-segment | Target Temperature |
|---|---|
| First 20 seconds | 250° C. |
| Next 40 seconds | 220° C. |
| Next 180 seconds | 230° C. |
| Next 20 seconds | 230° C. |
| Next 40 seconds | 220° C. |
| Thereafter | OFF |

When the information shown in Table 1 is received, the inhaler device 100 controls the temperature of the heater 121 in such a way that the temperature of the heater 121 reaches 250° C. in the first 20 seconds. Next, the inhaler device 100 controls the temperature of the heater 121 in such a way that the temperature of the heater 121 reaches 220° C. in the subsequent 40 seconds. The same applies to the other time sub-segments. Note that "Thereafter" and "OFF" in the last row of Table 1 indicate that heating is OFF in the corresponding time sub-segment. That is, the inhaler device 100 stops heating after the temperature control toward a target temperature of 220° C. in the last 40 seconds.

Information actually transmitted may be merely a combination of numerical values, including a numerical value representing a time sub-segment and a numerical value representing a target temperature in the time sub-segment.

For example, the information actually transmitted may be {(20, 250), (40, 220), (180, 230), (20, 230), (40, 220)}. The target temperature may be expressed in degrees Fahrenheit instead of degrees Celsius. "Thereafter" and "OFF" in the last row may be omitted.

Table 2 below shows an example of information representing the heating profile in FIG. 4 and transmitted by the first transmission method.

TABLE 2

Example of information representing heating profile transmitted by first transmission method

| Information of Time Sub-segment | Target Resistance |
| --- | --- |
| First 20 seconds | 1.50 Ω |
| Next 40 seconds | 1.20 Ω |
| Next 180 seconds | 1.30 Ω |
| Next 20 seconds | 1.30 Ω |
| Next 40 seconds | 1.20 Ω |
| Thereafter | OFF |

When the information shown in Table 2 is received, the inhaler device 100 controls the resistance of the heater 121 in such a way that the resistance of the heater 121 reaches 1.50Ω in the first 20 seconds. Next, the inhaler device 100 controls the resistance of the heater 121 in such a way that the resistance of the heater 121 reaches 1.20Ω in the subsequent 40 seconds. The same applies to the other time sub-segments. Note that "Thereafter" and "OFF" in the last row of Table 2 indicate that heating (or supply of electric power to the heater 121) is OFF in the corresponding time sub-segment. That is, the inhaler device 100 stops heating (or supply of electric power to the heater 121) after the resistance control toward a target resistance of 1.20Ω in the last 40 seconds.

Information actually transmitted may be merely a combination of numerical values, including a numerical value representing a time sub-segment and a numerical value representing a target resistance in the time sub-segment. For example, the information actually transmitted may be {(20, 1.50), (40, 1.20), (180, 1.30), (20, 1.30), (40, 1.20)}. "Thereafter" and "OFF" in the last row may be omitted.

Second Transmission Method

In a second transmission method, information representing a time sub-segment is information that represents the end of the time sub-segment as a period of time elapsed from the start time point of the heating profile. Also, information representing temporal change in parameter in the time sub-segment is information that represents a target value to be reached by the parameter in the time sub-segment. That is, the inhaler device 100 transmits information that includes, for each of a plurality of time sub-segments, a combination of information that represents the end of the time sub-segment as a period of time elapsed from the start time point and information that represents a target value to be reached by the parameter in the time sub-segment. A device, such as a terminal device, which is not the inhaler device 100, may transmit the information to the inhaler device 100.

Table 3 below shows an example of information representing the heating profile in FIG. 3 and transmitted by the second transmission method.

TABLE 3

Example of information representing heating profile transmitted by second transmission method

| Information of Time Sub-segment | Target Temperature |
| --- | --- |
| 20 seconds after heating start | 250° C. |
| 60 seconds after heating start | 220° C. |
| 240 seconds after heating start | 230° C. |
| 260 seconds after heating start | 230° C. |
| 300 seconds after heating start | 220° C. |
| Thereafter | OFF |

When the information shown in Table 3 is received, the inhaler device 100 controls the temperature of the heater 121 in such a way that the temperature of the heater 121 reaches 250° C. in 20 seconds after the heating start. Next, the inhaler device 100 controls the temperature of the heater 121 in such a way that the temperature of the heater 121 reaches 220° C. in 60 seconds after the heating start. The same applies to the other time sub-segments. Note that "Thereafter" and "OFF" in the last row of Table 3 indicate that heating is OFF in the corresponding time sub-segment. That is, the inhaler device 100 stops heating in 300 seconds after the heating start.

Information actually transmitted may be merely a combination of numerical values, including a numerical value representing a time sub-segment and a numerical value representing a target temperature in the time sub-segment. For example, the information actually transmitted may be {(20, 250), (60, 220), (240, 230), (260, 230), (300, 220)}. The target temperature may be expressed in degrees Fahrenheit instead of degrees Celsius. "Thereafter" and "OFF" in the last row may be omitted.

Table 4 below shows an example of information representing the heating profile in FIG. 4 and transmitted by the second transmission method.

TABLE 4

Example of information representing heating profile transmitted by second transmission method

| Information of Time Sub-segment | Target Resistance |
| --- | --- |
| 20 seconds after heating start | 1.50 Ω |
| 60 seconds after heating start | 1.20 Ω |
| 240 seconds after heating start | 1.30 Ω |
| 260 seconds after heating start | 1.30 Ω |
| 300 seconds after heating start | 1.20 Ω |
| Thereafter | OFF |

When the information shown in Table 4 is received, the inhaler device 100 controls the resistance of the heater 121 in such a way that the resistance of the heater 121 reaches 1.50Ω in 20 seconds after the heating start. Next, the inhaler device 100 controls the resistance of the heater 121 in such a way that the resistance of the heater 121 reaches 1.20Ω in 60 seconds after the heating start. The same applies to the other time sub-segments. Note that "Thereafter" and "OFF" in the last row of Table 4 indicate that heating (or supply of electric power to the heater 121) is OFF in the corresponding time sub-segment. That is, the inhaler device 100 stops heating (or supply of electric power to the heater 121) in 300 seconds after the heating start.

Information actually transmitted may be merely a combination of numerical values, including a numerical value representing a time sub-segment and a numerical value representing a target resistance in the time sub-segment. For example, the information actually transmitted may be {(20, 1.50), (60, 1.20), (240, 1.30), (260, 1.30), (300, 1.20)}. "Thereafter" and "OFF" in the last row may be omitted.

Third Transmission Method

In a third transmission method, information representing a time sub-segment is information that represents the beginning and end of the time sub-segment as periods of time elapsed from the start time point of the heating profile. Also, information representing temporal change in parameter in a time sub-segment is information that represents a target value to be reached by the parameter in the time sub-segment. That is, the inhaler device 100 transmits information that includes, for each of a plurality of time sub-segments, a combination of information that represents the beginning and end of the time sub-segment as periods of time elapsed from the start time point of the heating profile and information that represents a target value to be reached by the parameter in the time sub-segment. A device, such as a terminal device, which is not the inhaler device 100, may transmit the information to the inhaler device 100.

Table 5 below shows an example of information representing the heating profile in FIG. 3 and transmitted by the third transmission method.

TABLE 5

Example of information representing heating profile transmitted by third transmission method

| Time Sub-segment | Target Temperature |
|---|---|
| 0 to 20 seconds after heating start | 250° C. |
| 20 to 60 seconds after heating start | 220° C. |
| 60 to 240 seconds after heating start | 230° C. |
| 240 to 260 seconds after heating start | 230° C. |
| 260 to 300 seconds after heating start | 220° C. |
| Thereafter | OFF |

When the information shown in Table 5 is received, the inhaler device 100 controls the temperature of the heater 121 in such a way that the temperature of the heater 121 reaches 250° C. in 0 seconds to 20 seconds after the heating start. Next, the inhaler device 100 controls the temperature of the heater 121 in such a way that the temperature of the heater 121 reaches 220° C. in 20 seconds to 60 seconds after the heating start. The same applies to the other time sub-segments. Note that "Thereafter" and "OFF" in the last row of Table 5 indicate that heating is OFF in the corresponding time sub-segment. That is, the inhaler device 100 stops heating in 300 seconds after the heating start.

Information actually transmitted may be merely a combination of numerical values, including numerical values representing a time sub-segment and a numerical value representing a target temperature in the time sub-segment. For example, the information actually transmitted may be {(0, 20, 250), (20, 60, 220), (60, 240, 230), (240, 260, 230), (260, 300, 220)}. The target temperature may be expressed in degrees Fahrenheit instead of degrees Celsius. "Thereafter" and "OFF" in the last row may be omitted.

Table 6 below shows an example of information representing the heating profile in FIG. 4 and transmitted by the third transmission method.

TABLE 6

Example of information representing heating profile transmitted by third transmission method

| Time Sub-segment | Target Resistance |
|---|---|
| 0 to 20 seconds after heating start | 1.50 Ω |
| 20 to 60 seconds after heating start | 1.20 Ω |
| 60 to 240 seconds after heating start | 1.30 Ω |
| 240 to 260 seconds after heating start | 1.30 Ω |
| 260 to 300 seconds after heating start | 1.20 Ω |
| Thereafter | OFF |

When the information shown in Table 6 is received, the inhaler device 100 controls the resistance of the heater 121 in such a way that the resistance of the heater 121 reaches 1.50Ω in 0 seconds to 20 seconds after the heating start. Next, the inhaler device 100 controls the resistance of the heater 121 in such a way that the resistance of the heater 121 reaches 1.20Ω in 20 seconds to 60 seconds after the heating start. The same applies to the other time sub-segments. Note that "Thereafter" and "OFF" in the last row of Table 6 indicate that heating (or supply of electric power to the heater 121) is OFF in the corresponding time sub-segment. That is, the inhaler device 100 stops heating (or supply of electric power to the heater 121) in 300 seconds after the heating start.

Information actually transmitted may be merely a combination of numerical values, including numerical values representing a time sub-segment and a numerical value representing a target resistance in the time sub-segment. For example, the information actually transmitted may be {(0, 20, 1.50), (20, 60, 1.20), (60, 240, 1.30), (240, 260, 1.30), (260, 300, 1.20)}. "Thereafter" and "OFF" in the last row may be omitted.

Fourth Transmission Method

A fourth transmission method is a method that omits information representing temporal change in parameter in a time sub-segment. That is, as information representing the heating profile, the inhaler device 100 may transmit information from which information that represents temporal change in parameter in at least one of the time sub-segments is omitted. This configuration can further reduce the volume of communication.

Table 7 below shows an example of information representing the heating profile in FIG. 3 and transmitted by the fourth transmission method. A device, such as a terminal device, which is not the inhaler device 100, may transmit the information to the inhaler device 100.

TABLE 7

Example of information representing heating profile transmitted by fourth transmission method

| Time Sub-segment | Target Temperature |
|---|---|
| 0 to 20 seconds after heating start | 250° C. |
| 20 to 60 seconds after heating start | 220° C. |
| 60 to 240 seconds after heating start | 230° C. |
| 240 to 260 seconds after heating start | — |
| 260 to 300 seconds after heating start | 220° C. |
| Thereafter | OFF |

The receiving side may restore the omitted information in any manner. In an example, if the received information representing the heating profile does not include information that represents temporal change in parameter in a first time sub-segment, the inhaler device 100 may use information that represents temporal change in parameter in a second time sub-segment, which is immediately before the first time sub-segment, as information that represents temporal change in parameter in the first time sub-segment. For example, when the information shown in Table 7 is received, the inhaler device 100 controls the temperature of the heater 121 in such a way that the temperature of the heater 121 reaches 230° C. in 60 seconds to 240 seconds after the heating start. Then, the inhaler device 100 controls the temperature of the heater 121 in such a way that during the time sub-segment from 240 seconds to 260 seconds after the heating start, the temperature of the heater 121 remains at 230° C., which is a target temperature in the previous time sub-segment.

Information actually transmitted may be merely a combination of numerical values, including numerical values representing a time sub-segment and a numerical value representing a target temperature in the time sub-segment. For example, the information actually transmitted may be {(0, 20, 250), (20, 60, 220), (60, 240, 230), (240, 260, –), (260, 300, 220)}. The target temperature may be expressed in degrees Fahrenheit instead of degrees Celsius. "Thereafter" and "OFF" in the last row may be omitted.

Although Table 7 shows an example of adopting information that represents the time sub-segments used in the third transmission method, information that represents the time sub-segments used in the first transmission method or the second transmission method may be adopted.

Table 8 below shows an example of information representing the heating profile in FIG. 4 and transmitted by the fourth transmission method.

TABLE 8

Example of information representing heating profile transmitted by fourth transmission method

| Time Sub-segment | Target Resistance |
| --- | --- |
| 0 to 20 seconds after heating start | 1.50 Ω |
| 20 to 60 seconds after heating start | 1.20 Ω |
| 60 to 240 seconds after heating start | 1.30 Ω |
| 240 to 260 seconds after heating start | — |
| 260 to 300 seconds after heating start | 1.20 Ω |
| Thereafter | OFF |

The receiving side may restore the omitted information in any manner. In an example, if the received information representing the heating profile does not include information that represents temporal change in parameter in a first time sub-segment, the inhaler device 100 may use information that represents temporal change in parameter in a second time sub-segment, which is immediately before the first time sub-segment, as information that represents temporal change in parameter in the first time sub-segment. For example, when the information shown in Table 8 is received, the inhaler device 100 controls the resistance of the heater 121 in such a way that the resistance of the heater 121 reaches 1.30Ω in 60 seconds to 240 seconds after the heating start. Then, the inhaler device 100 controls the resistance of the heater 121 in such a way that during the time sub-segment from 240 seconds to 260 seconds after the heating start, the resistance of the heater 121 remains at 1.30Ω, which is a target resistance in the previous time sub-segment.

Information actually transmitted may be merely a combination of numerical values, including numerical values representing a time sub-segment and a numerical value representing a target resistance in the time sub-segment. For example, the information actually transmitted may be {(0, 20, 1.50), (20, 60, 1.20), (60, 240, 1.30), (240, 260, –), (260, 300, 1.20)}. "Thereafter" and "OFF" in the last row may be omitted.

Although Table 8 shows an example of adopting information that represents the time sub-segments used in the third transmission method, information that represents the time sub-segments used in the first transmission method or the second transmission method may be adopted.

Fifth Transmission Method

In a fifth transmission method, information representing temporal change in parameter in a time sub-segment is information that represents a function approximating the shape of temporal change in parameter in the time sub-segment. That is, the inhaler device 100 transmits information that includes, for each of a plurality of time sub-segments, a combination of information that represents the time sub-segment and information that represents a function approximating the shape of temporal change in parameter in the time sub-segment. A device, such as a terminal device, which is not the inhaler device 100, may transmit the information to the inhaler device 100. With this configuration, even when the heating profile has a complex shape, it is possible to reduce the volume of communication without substantial loss of information.

An example of the function approximating the shape of temporal change in parameter is a function F of time that represents a relation between time and target temperature, such as target temperature=F(time). Here, the time refers to a period of time elapsed from the start time point of the heating profile. An example of the information representing the function approximating the shape of temporal change in parameter is a coefficient of the function F.

Table 9 below shows an example of information representing the heating profile in FIG. 3 and transmitted by the fifth transmission method.

TABLE 9

Example of information representing heating profile transmitted by fifth transmission method

| Time Sub-segment | Coefficient p and Coefficient q of Function F |
| --- | --- |
| 0 to 20 seconds after heating start | p = p1, q = q1 |
| 20 to 60 seconds after heating start | p = p2, q = q2 |
| 60 to 240 seconds after heating start | p = p3, q = q3 |
| 240 to 260 seconds after heating start | p = p4, q = q4 |
| 260 to 300 seconds after heating start | p = p5, q = q5 |
| Thereafter | OFF |

Table 9 shows an example that includes, as information representing a function approximating the shape of temporal change in parameter, a coefficient p and a coefficient q of the function F that approximates the shape of temporal change in parameter. When the information shown in Table 9 is received, the inhaler device 100 controls the temperature of the heater 121 toward a target temperature which is a value obtained by substituting the received coefficients p and q and a period of time elapsed from the heating start into the function F. For example, the inhaler device 100 controls the temperature of the heater 121 in such a way that in 0 seconds to 20 seconds after the heating start, the same temperature as the target temperature represented by the function F that has p1 and q1 as the coefficients p and q, respectively, is attained by the heater 121. The same applies to the other time sub-segments. Note that "Thereafter" and "OFF" in the last row of Table 9 indicate that heating is OFF in the corresponding time sub-segment. That is, the inhaler device 100 stops heating in 300 seconds after the heating start.

Information actually transmitted may be merely a combination of numerical values, including numerical values representing a time sub-segment and coefficients of the function F. For example, the information actually transmitted may be {(0, 20, p1, q1), (20, 60, p2, q2), (60, 240, p3, q3), (240, 260, p4, q4), (260, 300, p5, q5)}. "Thereafter" and "OFF" in the last row may be omitted.

Although the function F has two coefficients in the example described above, the function F may have only one coefficient, or may have three or more coefficients. The function F may have a different number of coefficients for each time sub-segment. That is, the function may vary from one time sub-segment to another.

Although Table 9 shows an example of adopting information that represents the time sub-segments used in the third transmission method, information that represents the time sub-segments used in the first transmission method or the second transmission method may be adopted. Also, as in the fourth transmission method, as information representing the heating profile, the inhaler device 100 may transmit information from which information that represents temporal change in parameter in at least one of the time sub-segments is omitted. The method of restoration, described in association with the fourth transmission method, is also applicable here.

An example of the function approximating the shape of temporal change in parameter may be a function F of time that represents a relation between time and target resistance, such as target resistance=F(time). Here, the time refers to a period of time elapsed from the start time point of the heating profile. An example of the information representing the function approximating the shape of temporal change in parameter is a coefficient of the function F.

Table 10 below shows an example of information representing the heating profile in FIG. 4 and transmitted by the fifth transmission method.

TABLE 10

Example of information representing heating profile
transmitted by fifth transmission method

| Time Sub-segment | Coefficient r and Coefficient s of Function F |
|---|---|
| 0 to 20 seconds after heating start | r = r1, s = s1 |
| 20 to 60 seconds after heating start | r = r2, s = s2 |
| 60 to 240 seconds after heating start | r = r3, s = s3 |
| 240 to 260 seconds after heating start | r = r4, s = s4 |
| 260 to 300 seconds after heating start | r = r5, s = s5 |
| Thereafter | OFF |

Table 10 shows an example that includes, as information representing a function approximating the shape of temporal change in parameter, a coefficient r and a coefficient s of the function F that approximates the shape of temporal change in parameter. When the information shown in Table 10 is received, the inhaler device 100 controls the resistance of the heater 121 toward a target resistance which is a value obtained by substituting the received coefficients r and s and a period of time elapsed from the heating start into the function F. For example, the inhaler device 100 controls the resistance of the heater 121 in such a way that in 0 seconds to 20 seconds after the heating start, the same resistance as the target resistance represented by the function F that has r1 and s1 as the coefficients r and s, respectively, is attained by the heater 121. The same applies to the other time sub-segments. Note that "Thereafter" and "OFF" in the last row of Table 10 indicate that heating (or supply of electric power to the heater 121) is OFF in the corresponding time sub-segment. That is, the inhaler device 100 stops heating (or supply of electric power to the heater 121) in 300 seconds after the heating start.

Information actually transmitted may be merely a combination of numerical values, including numerical values representing a time sub-segment and coefficients of the function F. For example, the information actually transmitted may be {(0, 20, r1, s1), (20, 60, r2, s2), (60, 240, r3, s3), (240, 260, r4, s4), (260, 300, r5, s5)}. "Thereafter" and "OFF" in the last row may be omitted.

Although the function F has two coefficients in the example described above, the function F may have only one coefficient, or may have three or more coefficients. The function F may have a different number of coefficients for each time sub-segment. That is, the function may vary from one time sub-segment to another.

Although Table 10 shows an example of adopting information that represents the time sub-segments used in the third transmission method, information that represents the time sub-segments used in the first transmission method or the second transmission method may be adopted. Also, as in the fourth transmission method, as information representing the heating profile, the inhaler device 100 may transmit information from which information representing temporal change in parameter in at least one of the time sub-segments is omitted. The method of restoration, described in association with the fourth transmission method, is also applicable here.

(3) Heating Profile According to First Configuration Example

A method of discretizing and transmitting the heating profile according to the second configuration example has mainly been described with reference to FIG. 3. The present invention is similarly applicable to the heating profile according to the first configuration example.

Figure 5:
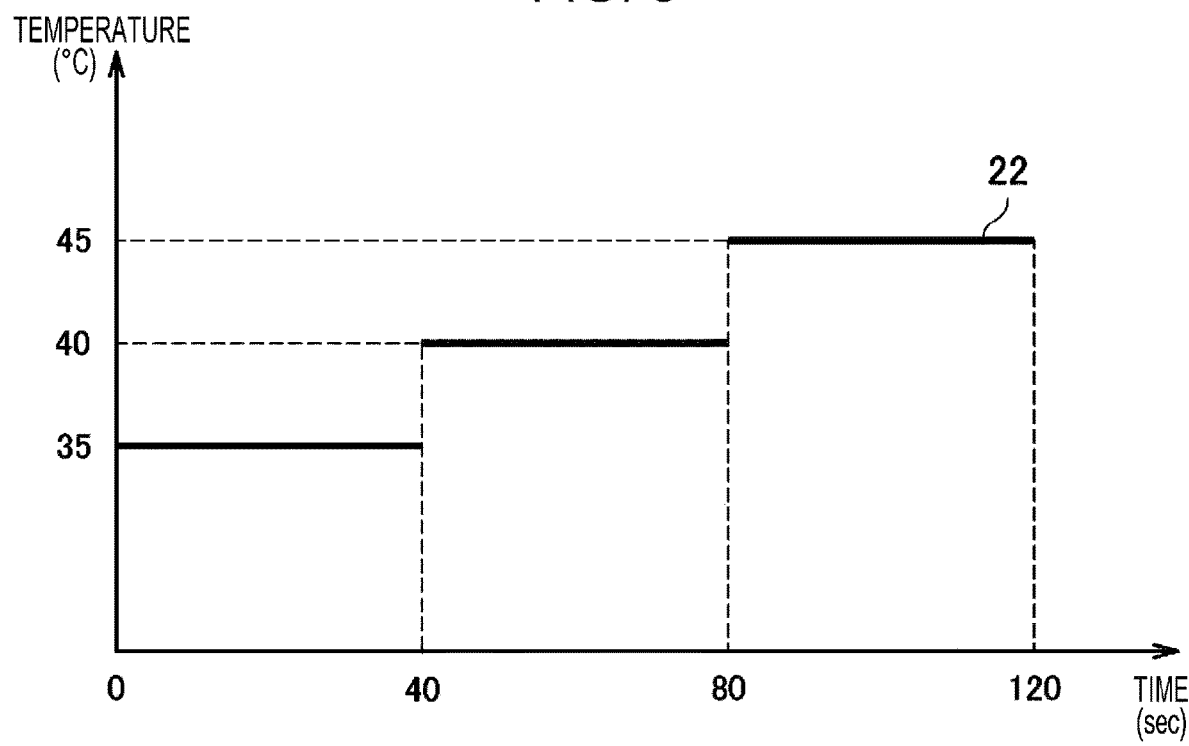
FIG. 5 is a graph showing an example of a heating profile that defines temporal changes of a target temperature according to the present embodiment.

First, an example of the heating profile according to the first configuration example will be described with reference to FIG. 5. FIG. 5 is a graph showing an example of a heating profile that defines temporal changes of a target temperature according to the present embodiment. The horizontal axis of the present graph represents time (in seconds). The start time point of the present heating profile is the time of detection of the first puff. That is, the horizontal axis of the present graph represents the time elapsed from the time of detection of the first puff. The vertical axis of the present graph represents the target temperature of the heater 121. A line 22 in the present graph represents the temporal changes of the target temperature in the heating profile.

Note that the line 22 represents the temporal changes of the target temperature for heating that is performed when a puff is detected. For example, when a puff is detected until the elapse of 40 seconds from the start time point, the inhaler device 100 controls the temperature of the heater 121 at a target temperature of 35° C. When a puff is detected after the elapse of 40 seconds and until the elapse of 80 seconds from the start time point, the inhaler device 100 controls the temperature of the heater 121 at a target temperature of 40° C. When a puff is detected after the elapse of 80 seconds and until the elapse of 120 seconds from the start time point, the inhaler device 100 controls the temperature of the heater 121 at a target temperature of 45° C.

The heating profile illustrated in FIG. 5 can also be transmitted by any of the first to fifth transmission methods. In an example, Table 11 below shows an example of information representing the heating profile in FIG. 5 and transmitted by the first transmission method.

TABLE 11

Example of information representing heating profile transmitted by first transmission method

| Information of Time Sub-segment | Target Temperature |
| --- | --- |
| First 40 seconds | 35° C. |
| Next 40 seconds | 40° C. |
| Next 40 seconds | 45° C. |
| Thereafter | OFF |

Figure 6:
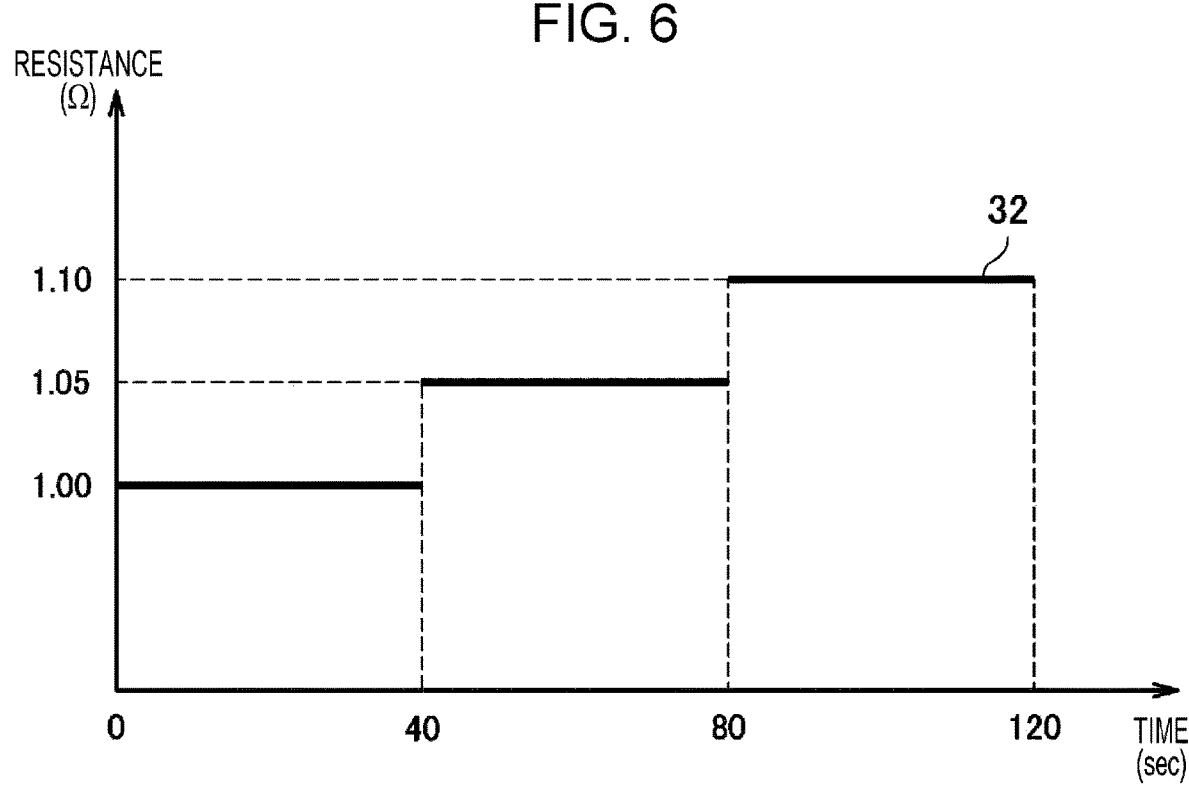
FIG. 6 is a graph showing an example of a heating profile that defines temporal changes of a target resistance according to the present embodiment.

As described above, when the electrical resistance of the heater 121 changes with the temperature of the heater 121, the heating profile may define the temporal changes of the target resistance. FIG. 6 is a graph showing an example of a heating profile that defines the temporal changes of a target resistance according to the present embodiment. The horizontal axis of the present graph represents time (in seconds). The vertical axis of the present graph represents the electrical resistance (i.e., target resistance) of the heater 121, in place of the target temperature of the heater 121 represented by the vertical axis in the example illustrated in FIG. 5. A line 32 in the present graph represents the temporal changes of the target resistance in the heating profile. The resistance represented by the vertical axis of the present graph is merely an example. Even the value of resistance corresponding to the same target temperature varies depending on the characteristics or ambient temperature of the heater 121.

The line 32 represents the temporal changes of the target resistance for heating that is performed when a puff is detected. For example, when a puff is detected until the elapse of 40 seconds from the start time point, the inhaler device 100 controls the resistance of the heater 121 at a target resistance of 1.00Ω. When a puff is detected after the elapse of 40 seconds and until the elapse of 80 seconds from the start time point, the inhaler device 100 controls the resistance of the heater 121 at a target resistance of 1.05Ω. When a puff is detected after the elapse of 80 seconds and until the elapse of 120 seconds from the start time point, the inhaler device 100 controls the resistance of the heater 121 at a target resistance of 1.10Ω.

The heating profile illustrated in FIG. 6 can also be transmitted by any of the first to fifth transmission methods. In an example, Table 12 below shows an example of information representing the heating profile in FIG. 6 and transmitted by the first transmission method.

TABLE 12

Example of information representing heating profile transmitted by first transmission method

| Information of Time Sub-segment | Target Resistance |
| --- | --- |
| First 40 seconds | 1.00 Ω |
| Next 40 seconds | 1.05 Ω |
| Next 40 seconds | 1.10 Ω |
| Thereafter | OFF |

Figure 7:
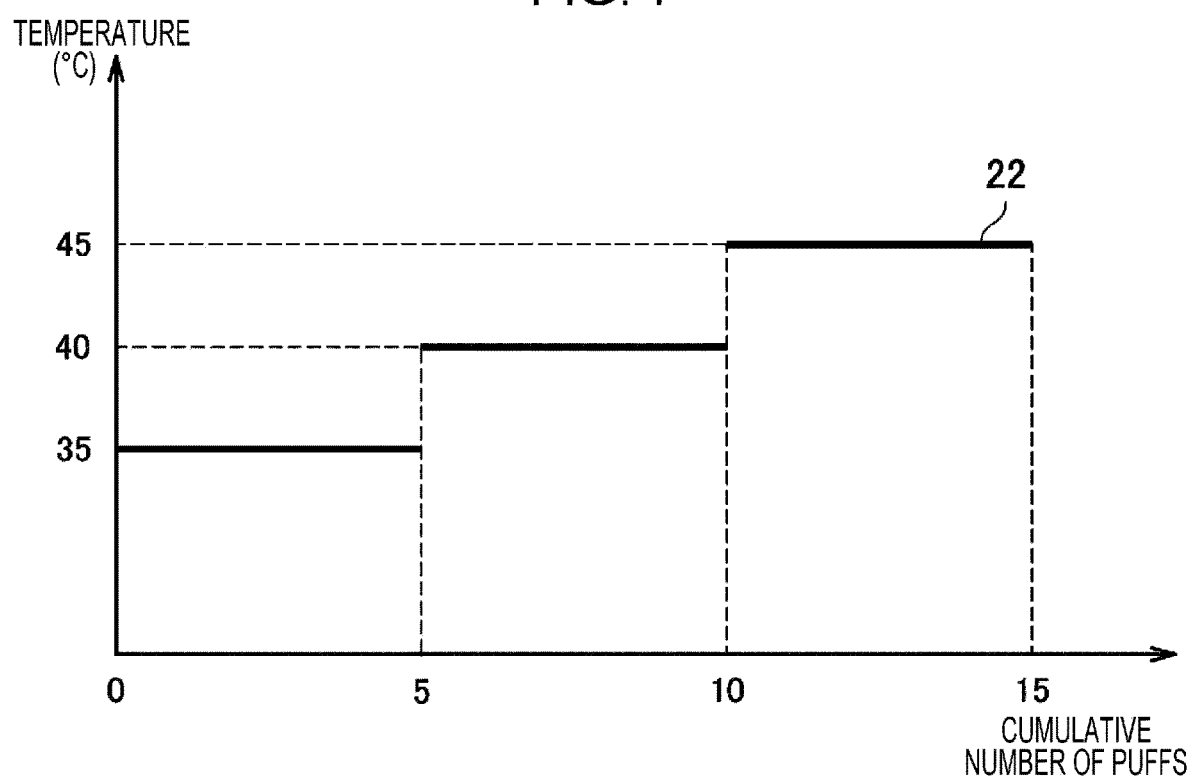
FIG. 7 is a graph showing an example of a heating profile that defines temporal changes of a target temperature according to the present embodiment.

The time segments in the heating profile according to the first configuration example may be defined by the number of puffs. An example of the heating profile in this case will now be described with reference to FIG. 7. FIG. 7 is a graph showing an example of a heating profile that defines temporal changes of a target temperature according to the present embodiment. The horizontal axis of the present graph represents the cumulative number of puffs. The start time point of the present heating profile is the time of detection of the first puff. That is, the horizontal axis of the present graph represents the cumulative number of puffs since the detection of the first puff. The vertical axis of the present graph represents the target temperature of the heater 121. The line 22 in the present graph represents the temporal changes of the target temperature in the heating profile.

Note that the line 22 represents the temporal changes of the target temperature for heating that is performed when a puff is detected. For example, before the cumulative number of puffs exceeds 5, the inhaler device 100 controls the temperature of the heater 121 at a target temperature of 35° C. in the case of detecting a puff. When the cumulative number of puffs is from 6 to 10, the inhaler device 100 controls the temperature of the heater 121 at a target temperature of 40° C. in the case of detecting a puff. When the cumulative number of puffs is from 11 to 15, the inhaler device 100 controls the temperature of the heater 121 at a target temperature of 45° C. in the case of detecting a puff.

The heating profile illustrated in FIG. 7 can also be transmitted by any of the first to fifth transmission methods. In an example, Table 13 below shows an example of information representing the heating profile in FIG. 7 and transmitted by the first transmission method.

TABLE 13

Example of information representing heating profile transmitted by first transmission method

| Information of Time Sub-segment | Target Temperature |
| --- | --- |
| First 5 puffs | 35° C. |
| Next 5 puffs | 40° C. |
| Next 5 puffs | 45° C. |
| Thereafter | OFF |

Figure 8:
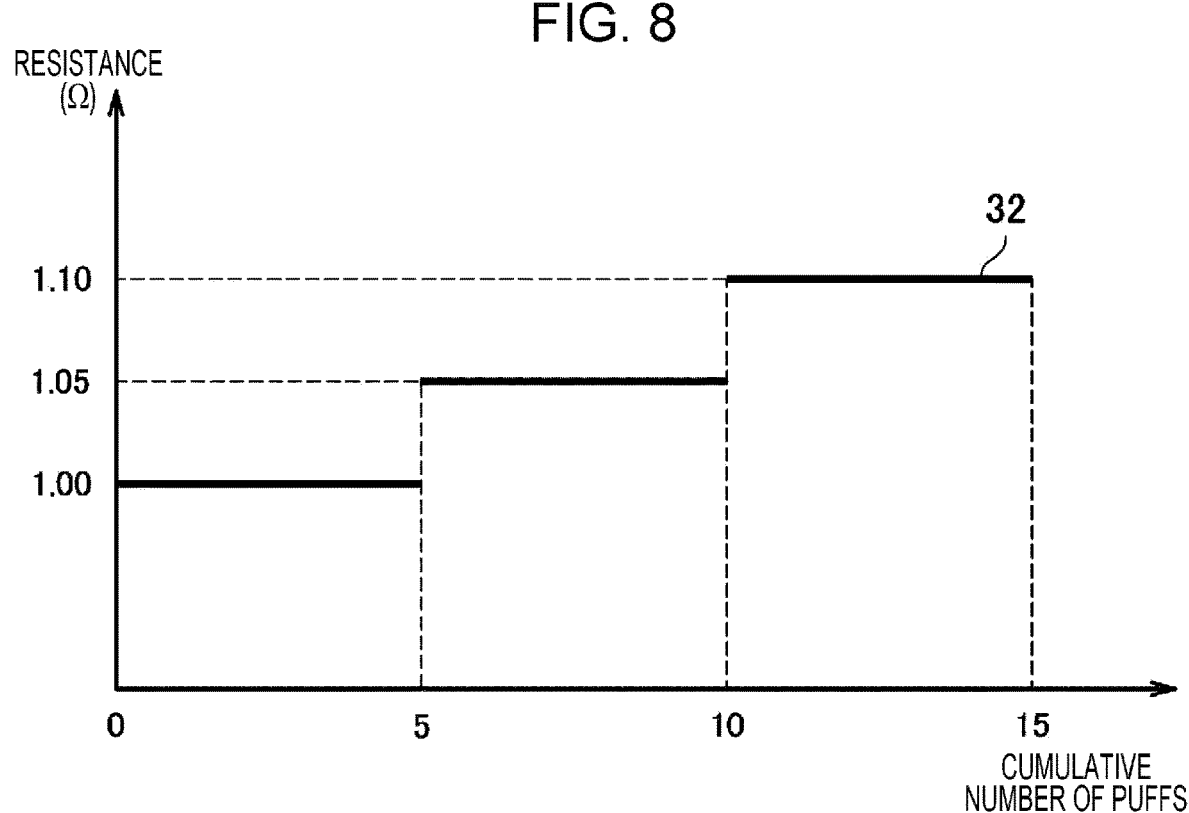
FIG. 8 is a graph showing an example of a heating profile that defines temporal changes of a target resistance according to the present embodiment.

As described above, when the electrical resistance of the heater 121 changes with the temperature of the heater 121, the heating profile may define the temporal changes of the target resistance. FIG. 8 is a graph showing an example of a heating profile that defines the temporal changes of a target resistance according to the present embodiment. The horizontal axis of the present graph represents time (in seconds). The vertical axis of the present graph represents the electrical resistance (i.e., target resistance) of the heater 121, in place of the target temperature of the heater 121 represented by the vertical axis in the example illustrated in FIG. 7. The line 32 in the present graph represents the temporal changes of the target resistance in the heating profile. The resistance represented by the vertical axis of the present graph is merely an example. Even the value of resistance corresponding to the same target temperature varies depending on the characteristics or ambient temperature of the heater 121.

The line 32 represents the temporal changes of the target resistance for heating that is performed when a puff is detected. For example, before the cumulative number of puffs exceeds 5, the inhaler device 100 controls the resistance of the heater 121 at a target resistance of 1.00Ω in the case of detecting a puff. When the cumulative number of puffs is from 6 to 10, the inhaler device 100 controls the resistance of the heater 121 at a target resistance of 1.05Ω in the case of detecting a puff. When the cumulative number of puffs is from 11 to 15, the inhaler device 100 controls the resistance of the heater 121 at a target resistance of 1.10Ω in the case of detecting a puff.

The heating profile illustrated in FIG. 8 can also be transmitted by any of the first to fifth transmission methods. In an example, Table 14 below shows an example of information representing the heating profile in FIG. 8 and transmitted by the first transmission method.

TABLE 14

Example of information representing heating profile
transmitted by first transmission method

| Information of Time Sub-segment | Target Resistance |
| --- | --- |
| First 5 puffs | 1.00 Ω |
| Next 5 puffs | 1.05 Ω |
| Next 5 puffs | 1.10 Ω |
| Thereafter | OFF |

(4) Flow of Processing

Figure 9:
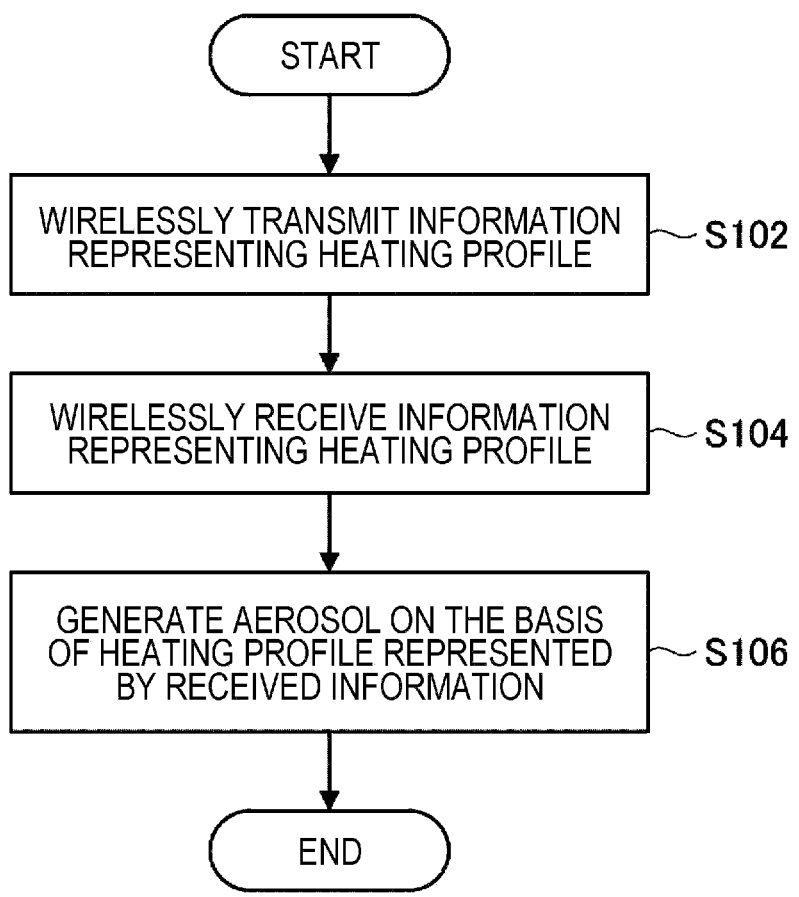
FIG. 9 is a flowchart illustrating an example of a flow of processing executed by an inhaler device according to the present embodiment.

FIG. 9 is a flowchart illustrating an example of a flow of processing executed by the inhaler device 100 according to the present embodiment.

As illustrated in FIG. 9, first, the inhaler device 100 wirelessly transmits information that represents a heating profile. The information is obtained by discretizing the heating profile (step S102). The information representing the heating profile is received, for example, by a user's terminal device and customized.

Next, the inhaler device 100 wirelessly receives information that represents a heating profile (step S104). For example, the information wirelessly received by the inhaler device 100 is information that represents a heating profile customized by the terminal device. The information is obtained by discretizing the customized heating profile.

Then, the inhaler device 100 generates an aerosol on the basis of the heating profile represented by the received information (step S106). Specifically, the inhaler device 100 controls the temperature of the heater 121 in such a way that the same temperature as the target temperature defined by the heating profile is attained by the heater 121.

3. Modification Examples

First Modification Example

In a first modification example, as information that represents a heating profile, the inhaler device 100 transmits and receives differential information (hereinafter also referred to as differential profile data) that represents a difference between an existing heating profile A recorded in the inhaler device 100 and a new heating profile B to be transmitted and received. The differential information is information that represents a part of the new heating profile B to be transmitted and received, different from the existing heating profile A recorded in the inhaler device 100. That is, of pieces of information representing differences between the existing heating profile A recorded in the inhaler device 100 and the new heating profile B to be transmitted and received, the differential information represents a part of the new heating profile B to be transmitted and received. A device, such as a terminal device, which is not the inhaler device 100, may transmit the differential profile data to the inhaler device 100. With this configuration, where only differential information is transmitted and received, a further reduction in communication volume is achieved. Also, by simply receiving differential information (differential profile data), the differential information is added to the existing heating profile A recorded therein, so that the inhaler device 100 can reproduce the new heating profile B to be transmitted and received.

Figure 10:
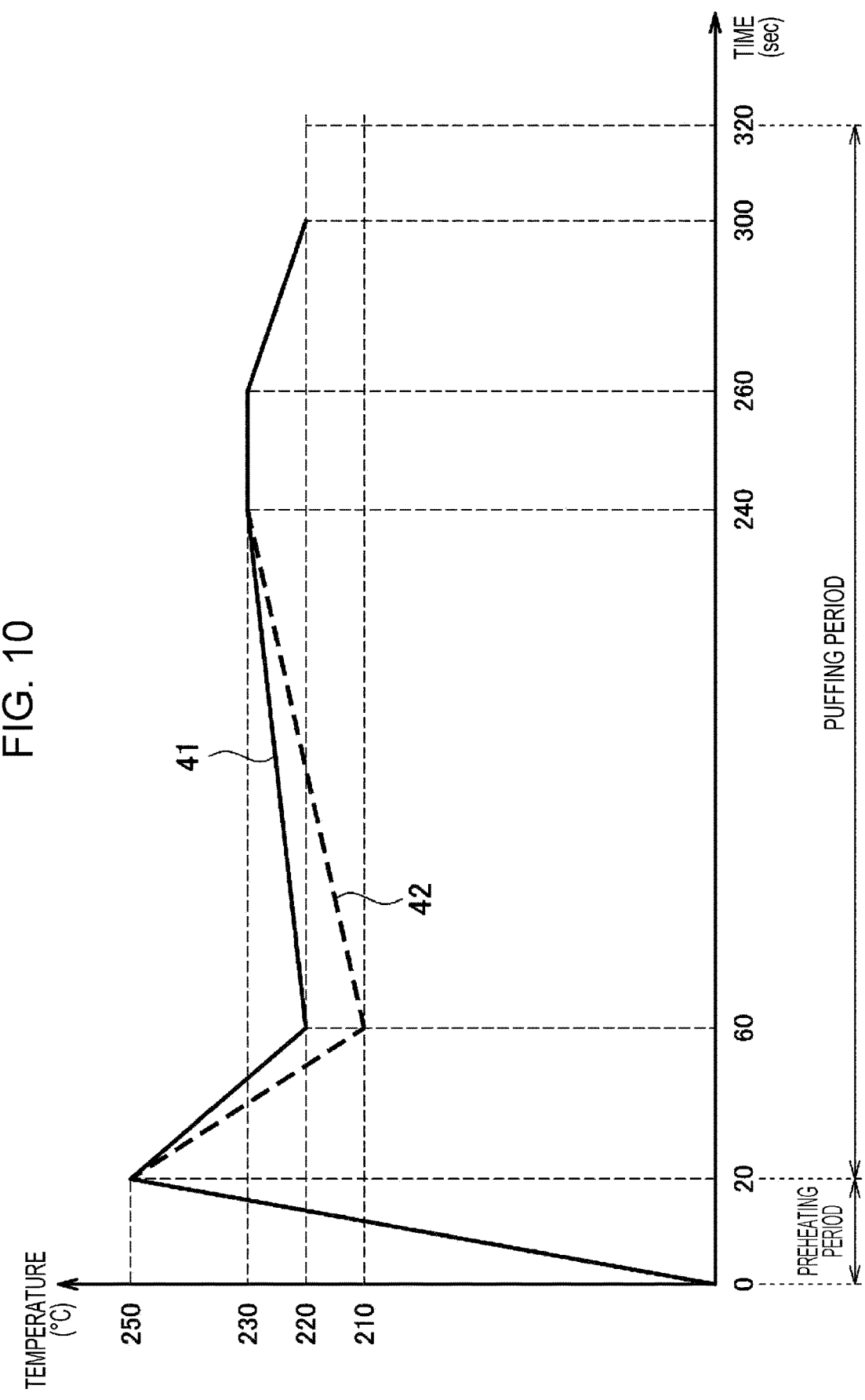
FIG. 10 is a graph showing an example of a heating profile that defines temporal changes of a target temperature according to a first modification example.

FIG. 10 is a graph showing an example of a heating profile that defines temporal changes of a target temperature according to the first modification example. The horizontal axis of the present graph represents time (in seconds). The vertical axis of the present graph represents the temperature of the heater 121. A line 41 in the present graph represents temporal changes of the target temperature in the existing heating profile A recorded in the inhaler device 100. A broken line 42 in the present graph represents temporal changes of the target temperature in the new heating profile B to be transmitted and received.

The line 41 in the present graph shows that the target temperature is set to reach 250° C. in 20 seconds after the heating start, reach 220° C. in 60 seconds after the heating start, reach 230° C. in 240 seconds after the heating start, remain at 230° C. until the elapse of 260 seconds after the heating start, and finally reach 220° C. in 300 seconds after the heating start.

The broken line 42 in the present graph shows that the target temperature is set to reach 250° C. in 20 seconds after the heating start (the broken line 42 is superimposed on the line 41 in FIG. 10), reach 210° C. in 60 seconds after the heating start, reach 230° C. in 240 seconds after the heating start, remain at 230° C. until the elapse of 260 seconds after the heating start (the broken line 42 is superimposed on the line 41 in FIG. 10), and finally reach 220° C. in 300 seconds after the heating start (the broken line 42 is superimposed on the line 41 in FIG. 10).

A comparison between the line 41 and the broken line 42 in the present graph shows that the existing heating profile A and the new heating profile B are the same, except that, in 60 seconds after the heating start, the target temperature in the new heating profile B is 210° C. while the target temperature in the existing heating profile A is 220° C. Of pieces of information representing differences between the existing heating profile A recorded in the inhaler device 100 and the new heating profile B to be transmitted and received, the differential information (differential profile data) represents a part of the new heating profile B different from the existing heating profile A. Therefore, the differential information (differential profile data) is "the target temperature is 210° C. in 60 seconds after the heating start".

The differential information (differential profile data) can also be transmitted by any of the first to fifth transmission methods. In an example, Table 15 below shows an example of information representing differential information (differential profile data) and transmitted by the second transmission method.

TABLE 15

Example of information representing differential
profile transmitted by second transmission method

| Information of Time Sub-segment | Target Temperature |
| --- | --- |
| 60 seconds after heating start | 210° C. |

Differential information (differential profile data) actually transmitted may be merely a combination of numerical values, including a numerical value representing a time sub-segment and a numerical value representing a target temperature in the time sub-segment. For example, the information actually transmitted may be {(60, 210)}. The target temperature may be expressed in degrees Fahrenheit instead of degrees Celsius.

The inhaler device 100 reproduces the new heating profile B from the existing heating profile A and the differential information (differential profile) received. In an example, the inhaler device 100 updates (or replaces) a part of the existing heating profile A corresponding to the differential information (differential profile) to reproduce the new heating profile B.

For example, in the existing heating profile A represented by the line 41 in FIG. 10, a part of the existing heating profile A corresponding to the differential information (differential profile) "the target temperature is 210° C. in 60 seconds after the heating start" is updated (or replaced) to reproduce the new heating profile B represented by the broken line 42 in FIG. 10. More specifically, the inhaler device 100 updates (or replaces) a part of the existing heating profile A corresponding to "the target temperature is 220° C. in 60 seconds after the heating start", with the differential information (differential profile) "the target temperature is 210° C. in 60 seconds after the heating start". On the other hand, the remaining part of the existing heating profile A, not corresponding to the differential information (differential profile), is considered unchanged and the values in the existing heating profile A are maintained without change by the inhaler device 100. Then, the inhaler device 100 combines the part of the existing heating profile A updated with the differential information (differential profile) and the remaining part of the existing heating profile A having the values kept unchanged, to form the new heating profile B.

Figure 11:
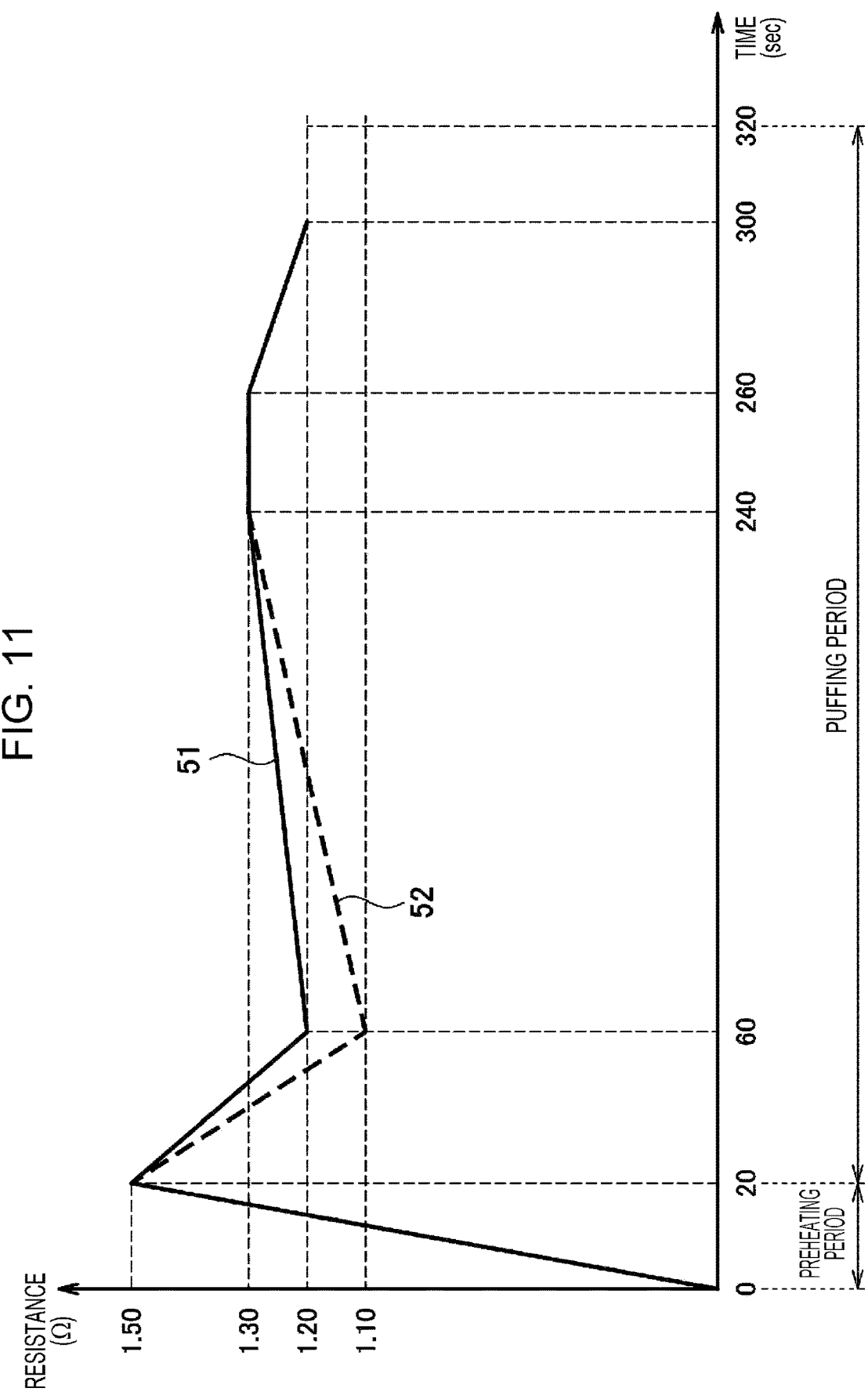
FIG. 11 is a graph showing an example of a heating profile that defines temporal changes of a target resistance according to the first modification example.

As described above, when the electrical resistance of the heater 121 changes with the temperature of the heater 121, the heating profile may define the temporal changes of the target resistance. FIG. 11 is a graph showing an example of a heating profile that defines temporal changes of a target resistance according to the first modification example. The horizontal axis of the present graph represents time (in seconds). The vertical axis of the present graph represents the electrical resistance (i.e., target resistance) of the heater 121, in place of the target temperature of the heater 121 represented by the vertical axis in the example illustrated in FIG. 10. A line 51 in the present graph represents temporal changes of the target resistance in the existing heating profile A recorded in the inhaler device 100. A broken line 52 in the present graph represents temporal changes of the target resistance in the heating profile B to be transmitted and received. The resistance represented by the vertical axis of the present graph is merely an example. Even the value of resistance corresponding to the same target temperature varies depending on the characteristics or ambient temperature of the heater 121.

The line 51 in the present graph shows that the target resistance is set to reach 1.50Ω in 20 seconds after the heating start, reach 1.20Ω in 60 seconds after the heating start, reach 1.30Ω in 240 seconds after the heating start, remain at 1.30Ω until the elapse of 260 seconds after the heating start, and finally reach 1.20Ω in 300 seconds after the heating start.

The broken line 52 in the present graph shows that the target resistance is set to reach 1.50Ω in 20 seconds after the heating start (the broken line 52 is superimposed on the line 51 in FIG. 11), reach 1.10Ω in 60 seconds after the heating start, reach 1.30Ω in 240 seconds after the heating start, remain at 1.30Ω until the elapse of 260 seconds after the heating start (the broken line 52 is superimposed on the line 51 in FIG. 11), and finally reach 1.20Ω in 300 seconds after the heating start (the broken line 52 is superimposed on the line 51 in FIG. 11).

A comparison between the line 51 and the broken line 52 in the present graph shows that the existing heating profile A and the new heating profile B are the same, except that, in 60 seconds after the heating start, the target resistance in the new heating profile B is 1.10Ω while the target resistance in the existing heating profile A is 1.20Ω Of pieces of information representing differences between the existing heating profile A recorded in the inhaler device 100 and the new heating profile B to be transmitted and received, the differential information (differential profile data) represents a part of the new heating profile B different from the existing heating profile A. Therefore, the differential information (differential profile data) is "the target resistance is 1.10Ω in 60 seconds after the heating star".

The differential information (differential profile data) can also be transmitted by any of the first to fifth transmission methods. In an example, Table 16 below shows an example of information representing differential information (differential profile data) and transmitted by the second transmission method.

TABLE 16

Example of information representing differential profile transmitted by second transmission method

| Information of Time Sub-segment | Target Resistance |
|---|---|
| 60 seconds after heating start | 1.10 Ω |

Differential information (differential profile data) actually transmitted may be merely a combination of numerical values, including a numerical value representing a time sub-segment and a numerical value representing a target resistance in the time sub-segment. For example, the information actually transmitted may be {(60, 1.10)}.

The inhaler device 100 reproduces the new heating profile B from the existing heating profile A and the differential information (differential profile) received. In an example, the inhaler device 100 updates (or replaces) a part of the existing heating profile A corresponding to the differential information (differential profile) to reproduce the new heating profile B.

Second Modification Example

In a second modification example, the inhaler device 100 transmits and receives coded profile data as information that represents a heating profile. In the second modification example, information representing the heating profile is coded profile data generated by conversion using a common table that associates each parameter candidate in a time sub-segment with the corresponding code, such as an alphanumeric character. That is, in the second modification example, information representing the heating profile is expressed as coded profile data by a plurality of codes included in the common table. With this configuration, where coded profile data including codes with a small data volume is transmitted and received, a further reduction in communication volume is achieved.

A common table is held by the inhaler device 100 and a device, such as a terminal device, which is not the inhaler device 100. The device, such as a terminal device, which is not the inhaler device 100, transmits and receives a heating profile to and from the inhaler device 100. When transmitting information representing the heating profile, the inhaler device 100 or the device, such as a terminal device, which is not the inhaler device 100, refers to the common table held therein to convert a parameter included in the heating profile to a code and generate coded profile data. The inhaler device 100 or the device, such as a terminal device, which is not the inhaler device 100, transmits the generated coded profile. When receiving coded profile data, on the other hand, the inhaler device 100 or the device, such as a terminal device, which is not the inhaler device 100, refers to the common table held therein to convert the coded profile data to a parameter and reproduce the heating profile.

FIG. 12 is a diagram illustrating an example of a common table that defines target temperatures according to the second modification example. Columns of the present table provide information representing time sub-segments, which are assigned with respective codes, such as a, b, and c. Rows of the present table provide target temperatures, which are assigned with respective codes, such as 1, 2, and 3. Each cell of the present table is provided with 0 or 1. The value 0 means that the cell is not selected, and the value 1 means that the cell is selected.

Figure 13:
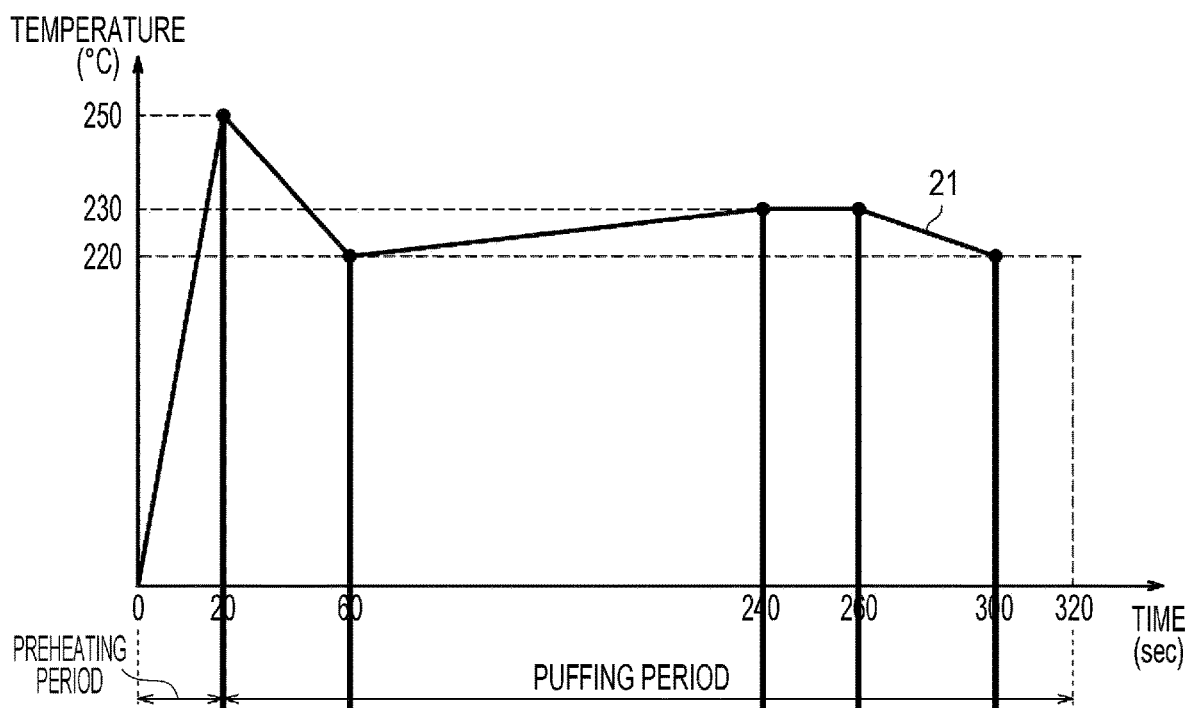
FIG. 13 is a diagram illustrating an example of a correspondence between the common table illustrated in FIG. 12 and a heating profile.

FIG. 13 is a diagram illustrating an example of a correspondence between the common table illustrated in FIG. 12 and a heating profile. As illustrated in FIG. 13, each time sub-segment in the heating profile is associated with a column of the common table. In the example illustrated in FIG. 13, the time sub-segment "20 seconds after the heating start" is associated with code a in the common table. A cell at the intersection of each time sub-segment in the heating profile and a target temperature in the time sub-segment is provided with 1 indicating that the cell is selected. In the example illustrated in FIG. 13, a cell at the intersection of code a associated with "20 seconds" and code 6 associated with the target temperature 250° C. in the common table is provided with 1. Similarly, in the example illustrated in FIG. 13, a cell at the intersection of code c and code 3, a cell at the intersection of code 1 and code 4, a cell at the intersection of code m and code 4, and a cell at the intersection of code p and code 3 are provided with 1 indicating that the cell is selected.

In the second modification example, information representing the heating profile is expressed as coded profile data that includes a plurality of combinations of codes in the columns and rows corresponding to cells of the common table that are each provided with 1 indicating that the cell is selected. For example, in the example illustrated in FIG. 13, information representing the heating profile is coded profile data that includes a6, c3, 14, m4, and p3, each of which is a combination of codes in the column and row of a cell provided with 1 indicating that the cell is selected.

Coded profile data actually transmitted is a combination of codes, and is merely a combination of alphanumeric characters. For example, information actually transmitted is {a6, c3, 14, m4, p3}.

When coded profile data is received, the inhaler device 100 or a device, such as a terminal device, which is not the inhaler device 100, refers to the common table held therein to convert the coded profile data to a parameter and reproduce the heating profile. For example, when {a6, c3, 14, m4, p3} is received as coded profile data, the inhaler device 100 refers to the common table illustrated as an example in FIG. 12 to convert a6 to "the target temperature is 250° C. in 20 seconds after the heating start", convert c3 to "the target temperature is 220° C. in 60 seconds after the heating start", convert 14 to "the target temperature is 230° C. in 240 seconds after the heating start", convert m4 to "the target temperature is 230° C. in 260 seconds after the heating start", and convert p3 to "the target temperature is 220° C. in 300 seconds after the heating start" and reproduce the heating profile.

In the example illustrated in FIG. 12, each row of the common table represents the temperature of the heater 121. When the electrical resistance of the heater 121 changes with the temperature of the heater 121, however, each row of the common table may represent the resistance of the heater 121. FIG. 14 is a diagram illustrating an example of a common table that defines target resistances according to the second modification example. Columns of the present table provide information representing time sub-segments, which are assigned with respective codes, such as a, b, and c. Rows of the present table provide target resistances, which are assigned with respective codes, such as 1, 2, and 3. Each cell of the present table is provided with 0 or 1. The value 0 means that the cell is not selected, and the value 1 means that the cell is selected.

Figure 15:
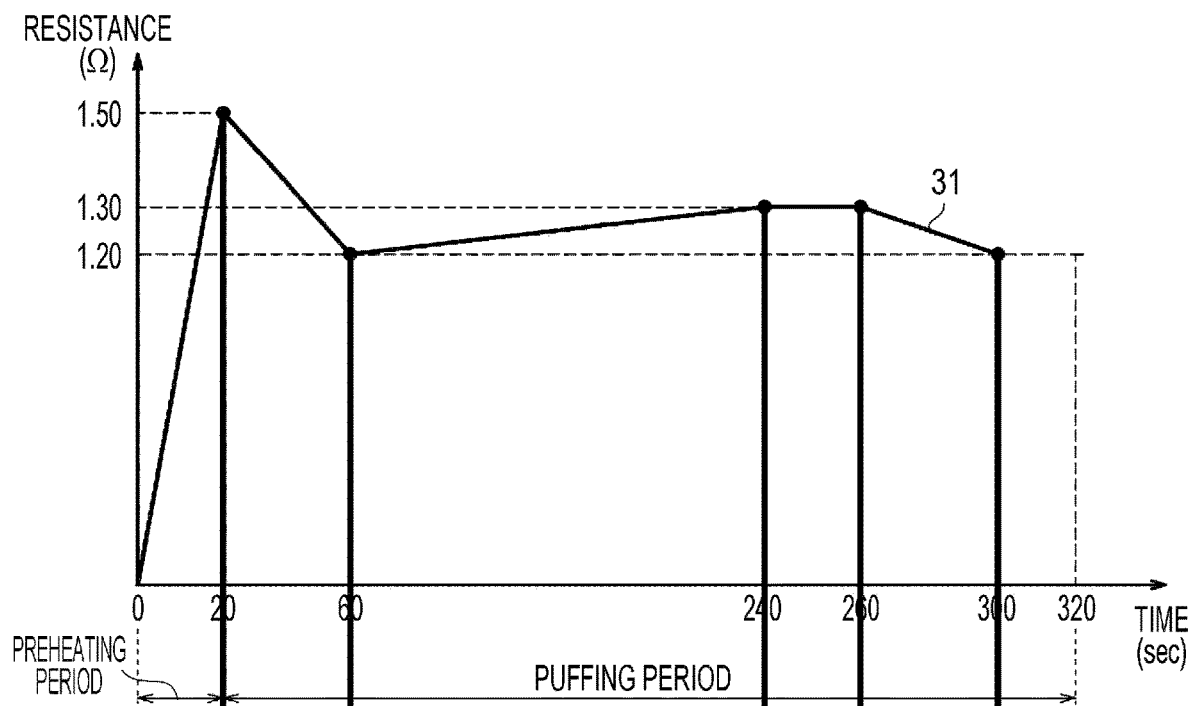
FIG. 15 is a diagram illustrating an example of a correspondence between the common table illustrated in FIG. 14 and a heating profile.

FIG. 15 is a diagram illustrating an example of a correspondence between the common table illustrated in FIG. 14 and a heating profile. As illustrated in FIG. 15, each time sub-segment in the heating profile is associated with a column of the common table. In the example illustrated in FIG. 15, the time sub-segment "20 seconds after the heating start" is associated with code a in the common table. A cell at the intersection of each time sub-segment in the heating profile and a target resistance in the time sub-segment is provided with 1 indicating that the cell is selected. In the example illustrated in FIG. 15, a cell at the intersection of code a associated with "20 seconds" and code 6 associated with the target resistance 1.50Ω in the common table is provided with 1. Similarly, in the example illustrated in FIG. 15, a cell at the intersection of code c and code 3, a cell at the intersection of code 1 and code 4, a cell at the intersection of code m and code 4, and a cell at the intersection of code p and code 3 are provided with 1 indicating that the cell is selected.

In the second modification example, information representing the heating profile is expressed as coded profile data that includes a plurality of combinations of codes in the columns and rows corresponding to cells of the common table that are each provided with 1 indicating that the cell is selected. For example, in the example illustrated in FIG. 14, information representing the heating profile is coded profile data that includes a6, c3, 14, m4, and p3, each of which is a combination of codes in the column and row of a cell provided with 1 indicating that the cell is selected.

Coded profile data actually transmitted is a combination of codes, and is merely a combination of alphanumeric characters. For example, information actually transmitted is {a6, c3, 14, m4, p3}.

When coded profile data is received, the inhaler device 100 or a device, such as a terminal device, which is not the inhaler device 100, refers to the common table held therein to convert the coded profile data to a parameter and reproduce the heating profile. For example, when {a6, c3, 14, m4, p3} is received as coded profile data, the inhaler device 100 refers to the common table illustrated as an example in FIG. 14 to convert a6 to "the target resistance is 1.50Ω in 20 seconds after the heating start", convert c3 to "the target resistance is 1.20Ω in 60 seconds after the heating start", convert 14 to "the target resistance is 1.30Ω in 240 seconds after the heating start", convert m4 to "the target resistance is 1.30Ω in 260 seconds after the heating start", and convert p3 to "the target resistance is 1.20Ω in 300 seconds after the heating start" and reproduce the heating profile.

4. Supplemental Remarks

While preferred embodiments of the present invention have been described in detail with reference to the accompanying drawings, the present invention is not limited to such examples. It is obvious that a person with ordinary knowledge in the technical field to which the present invention pertains can make various changes or modifications within the technical ideas set forth in the claims, and it is to be understood that these changes and modifications are to be embraced by the technical scope of the present invention.

For example, the embodiments described above refer to an example where the parameter in the heating profile according to the first configuration example and the second configuration example is the temperature of the heater 121. However, the present invention is not limited to such an example. For example, the parameter may be the temperature of a region heated by the heater 121. Examples of the region heated by the heater 121 include the holder 140. In this case, the controller 116 controls the supply of electric power to the heater 121 in such a way that the same temperature as the target temperature defined by the heating profile is attained in the holder 140. In another example, the parameter may be information related to electricity supplied to the heater 121. For example, the parameter may be voltage, current, resistance, or electric power supplied to the heater 121. In this case, the controller 116 controls the supply of electric power to the heater 121 in such a way that voltage, current, resistance, or electric power which is the same as that defined by the heating profile is supplied to the heater 121.

The heating profile described above is an example of a profile which is information related to an operation performed by the inhaler device 100 to generate an aerosol. The inhaler device 100 may transmit and receive another profile, different from the heating profile, as discrete data obtained by discretizing the profile using the technique described in the embodiments. For example, the profile, different from the heating profile, may be information that represents a result of operation performed by the inhaler device 100 to generate an aerosol (hereinafter also referred to as an operation result profile). The parameter in the operation result profile is information detected when the inhaler device 100 performs the operation of generating an aerosol, that is, information detected when the heater 121 operates. For example, although the heating profile is information that represents changes of a target temperature, the operation result profile may be information that represents changes of an actual temperature. The operation result profile can also be transmitted and received by any of the first to fifth transmission methods. With this configuration, the inhaler device 100 can reduce the volume of communication in both transmitting and receiving the operation result profile, without substantial loss of information.

Examples of the parameter in the operation result profile include, as in the heating profile, the temperature of the heater 121, the temperature of a region heated by the heater 121, and information related to electricity supplied to heater 121. The parameter in the operation result profile may be the amount of the aerosol inhaled by the user after being generated by the heater 121 (hereinafter also referred to as the amount of aerosol delivery). In this case, the sensor 112, which serves as a sensor for detecting the amount of aerosol delivery, includes a filter that collects aerosol and a component analyzer that analyzes the components of the collected aerosol. The amount of aerosol delivery may be the amount of main aerosol components per puff, delivered to the oral cavity of the user. The main aerosol components are visible aerosol components generated when various aerosol sources included in the substrate are heated at a predetermined temperature or higher. Typically, the aerosol sources included in the substrate are propylene glycol and glycerine. When the substrate contains a flavor source, such as tobacco, an aerosol component derived from the flavor source is also included in the main aerosol components.

In the embodiments described above, transmission and reception of information representing the heating profile may be transmission and reception of information that combines the information representing the heating profile with other information. For example, information representing the heating profile may be transmitted and received as information that combines the information representing the heating profile with information related to the heating profile. The information related to the heating profile is, for example, a correction value used to correct the heating profile on the basis of the characteristics of the heater 121 of each inhaler device 100.

In the embodiments described above, information representing the heating profile may be included in, for example, firmware of the inhaler device 100. That is, the firmware transmitted and received by the inhaler device 100 may include information representing the heating profile described in the embodiments. In this case, by transmitting and receiving firmware, the inhaler device 100 can transmit and receive information representing the heating profile. For example, when updating firmware, the inhaler device 100 may receive information representing the heating profile, described in the embodiments, as part of the firmware to be updated.

The series of processes carried out by each of the devices described in the present specification may be implemented by software, hardware, or a combination of software and hardware. Programs constituting the software are stored in advance, for example, in a recording medium (non-transitory medium) inside or outside the device. For example, each of the programs is loaded into a RAM during execution by a computer and is executed by a processor, such as a CPU. Examples of the recording medium include a magnetic disk, an optical disc, a magneto-optical disk, and a flash memory. The computer program described above may be distributed, for example, via a network without using such a recording medium.

The processing described with reference to the flowchart and the sequence diagrams in the present specification does not necessarily need to be executed in the illustrated order. Some processing steps may be executed in parallel. Additional processing steps may be adopted, and some processing steps may be omitted.

The configurations described below are also within the technical scope of the present invention.

(1)

An inhaler device includes a controller configured to control an operation of a heater that heats a substrate to generate an aerosol, and a communicator configured to wirelessly transmit information. The communicator transmits the information as information representing a profile that is information representing temporal changes in parameter related to the operation of the heater in a period from a (1)

start time point to an end time point. The information transmitted by the communicator includes, for each of a plurality of time segments constituting the period from the start time point to the end time point, a combination of information representing the time segment and information representing temporal change in parameter in the time segment.

(2)

In the inhaler device described in (1), the information representing the time segment is information that represents a sequential position of the time segment and a length of the time segment.

(3)

In the inhaler device described in (1), the information representing the time segment is information that represents an end of the time segment as a period of time elapsed from the start time point.

(4)

In the inhaler device described in (1), the information representing the time segment is information that represents each of a beginning and an end of the time segment as a period of time elapsed from the start time point.

(5)

In the inhaler device described in any one of (1) to (4), the information representing temporal change in parameter in the time segment is information that represents a target value to be reached by the parameter in the time segment.

(6)

In the inhaler device described in any one of (1) to (4), the information representing temporal change in parameter in the time segment is information that represents a function approximating a shape of the temporal change in parameter in the time segment.

(7)

In the inhaler device described in any one of (1) to (6), as the information representing the profile, the communicator transmits information from which information representing temporal change in parameter in at least one of the time segments is omitted.

(8)

In the inhaler device described in any one of (1) to (7), the parameter is information that defines an operation performed by the heater to heat the substrate, and the controller performs control to cause the heater to operate in accordance with the profile.

(9)

In the inhaler device described in (7), if the information representing the profile received does not include information representing temporal change in parameter in a first time segment, the controller uses information representing temporal change in parameter in a second time segment as information representing temporal change in parameter in the first time segment. The second time segment is one time segment before the first time segment.

(10)

In the inhaler device described in any one of (1) to (9), the parameter is information detected when the heater operates.

(11)

In the inhaler device described in any one of (1) to (10), the parameter is a temperature of the heater.

(12)

In the inhaler device described in any one of (1) to (10), the parameter is a temperature of a region heated by the heater.

(13)

In the inhaler device described in any one of (1) to (10), the parameter relates to electricity supplied to the heater.

(14)

In the inhaler device described in (10), the parameter is the amount of the aerosol inhaled by a user. The aerosol is generated by the heater.

(15)

In the inhaler device described in any one of (1) to (14), the communicator transmits the information representing the profile through NFC.

(16)

An information transmission method includes wirelessly transmitting information. The information is wirelessly transmitted as information representing a profile that is information representing temporal changes in parameter related to an operation of a heater configured to heat a substrate to generate an aerosol in a period from a start time point to an end time point. The information wirelessly transmitted includes, for each of a plurality of time segments constituting the period from the start time point to the end time point, a combination of information representing the time segment and information representing temporal change in parameter in the time segment.

(17)

A program causes a computer to control an inhaler device that controls an operation of a heater configured to heat a substrate to generate an aerosol. The program causes the computer to control the inhaler device in such a way that the inhaler device wirelessly transmits information as information representing a profile that is information representing temporal changes in parameter related to the operation of the heater for heating the substrate to generate an aerosol in a period from a start time point to an end time point. The information wirelessly transmitted includes, for each of a plurality of time segments constituting the period from the start time point to the end time point, a combination of information representing the time segment and information representing temporal change in parameter in the time segment.

REFERENCE SIGNS LIST 100 inhaler device
110 power supply unit
111 power supply
112 sensor
113 notifier
114 memory
115 communicator
116 controller
120 cartridge
121 heater
122 liquid guide
123 liquid storage
124 mouthpiece
130 flavor imparting cartridge
131 flavor source
140 holder
141 internal space
142 opening
143 bottom
144 heat insulator
150 stick substrate
151 substrate
152 inhalation port
180 airflow path
181 air inlet hole
182 air outlet hole

The invention claimed is:

1. An inhaler device comprising:
a heater configured to heat a substrate to generate an aerosol;
a communicator configured to receive, through a communication link, information indicating a profile defining an operation of the heater; and
a controller configured to control the operation of the heater in accordance with the information representing the profile,
wherein the information representing the profile includes a combination of information representing time and information representing a parameter related to the operation of the heater at the time, and
wherein if the information representing the profile received does not include information representing a target value of the parameter related to the operation of the heater in a first time period, the controller uses information representing a target value of the parameter related to the operation of the heater in a second time period as the information representing the target value of the parameter related to the operation of the heater in the first time period, the second time period being one time period before the first time period.

2. The inhaler device according to claim 1, wherein the profile is information that represents temporal changes in parameter related to the operation of the heater in a period from a start time point to an end time point; and
the information representing the time is information that represents each of a plurality of time segments constituting the period from the start time point to the end time point.

3. The inhaler device according to claim 2, wherein the information representing the plurality of time segments is information that represents a sequential position of the time segment and a length of the time segment, respectively.

4. The inhaler device according to claim 2, wherein the information representing the plurality of time segments is information that represents an end of the time segment as a period of time elapsed from the start time point, respectively.

5. The inhaler device according to claim 2, wherein the information representing the plurality of time segments is information that represents each of a beginning and an end of the time segment as a period of time elapsed from the start time point, respectively.

6. The inhaler device according to claim 1, wherein the information representing the parameter related to the operation of the heater is information that represents a target value to be reached by the parameter at the time.

7. The inhaler device according to claim 1, wherein the information representing the profile is information that represents temporal changes in parameter related to the operation of the heater in a period from a start time point to an end time point; and
the information representing the parameter related to the operation of the heater is information that represents temporal change in parameter at the time.

8. The inhaler device according to claim 7, wherein the information that represents temporal change in parameter is information that represents a function approximating a shape of the temporal change in parameter at the time.

9. The inhaler device according to claim 1, wherein the profile is information that represents temporal changes in parameter related to the operation of the heater in a period from a start time point to an end time point;
the information representing the time is information that represents each of a plurality of time segments constituting the period from the start time point to the end time point;
the information representing the parameter related to the operation of the heater is information that represents temporal change in parameter in the time segment; and
the communicator receives, through the communication link, information that includes, for each of the plurality of time segments constituting the period from the start time point to the end time point, a combination of information representing the time segment and information representing temporal change in parameter in the time segment.

10. The inhaler device according to claim 1, wherein as the information representing the profile, the communicator transmits information from which information representing a target value of the parameter related to the operation of the heater in at least part of the time is omitted.

11. The inhaler device according to claim 1, wherein the parameter is information detected when the heater operates.

12. The inhaler device according to claim 1, wherein the parameter is a temperature of the heater, or a resistance of the heater.

13. The inhaler device according to claim 1, wherein the parameter is a temperature of a region heated by the heater.

14. The inhaler device according to claim 1, wherein the parameter relates to electricity supplied to the heater.

15. The inhaler device according to claim 1, wherein the parameter is the amount of the aerosol inhaled by a user, the aerosol being generated by the heater.

16. The inhaler device according to claim 1, wherein the communication link is wireless.

17. The inhaler device according to claim 1, wherein the communicator transmits the information representing the profile through NFC.

18. A controlling method comprising:
receiving through a communication link, information representing a profile defining an operation of a heater configured to heat a substrate to generate an aerosol, and
controlling the operation of the heater in accordance with the information representing the profile,
wherein the information representing the profile includes a combination of information representing time and information representing a parameter related to the operation of the heater at the time, and
wherein the controlling includes if the information representing the profile received does not include information representing a target value of the parameter related to the operation of the heater in a first time period, using information representing a target value of the parameter related to the operation of the heater in a second time period as the information representing the target value of the parameter related to the operation of the heater in the first time period, the second time period being one time period before the first time period.

19. A non-transitory computer readable medium having a program stored therein, the program causing a computer to control an inhaler device that controls an operation of a heater configured to heat a substrate to generate an aerosol, the program causing the computer to control the inhaler device in such a way that through a communication link, the inhaler device receives, as information representing a profile defining the operation of the heater for heating the substrate to generate an aerosol, a combination of information representing time and information representing a parameter related to the operation of the heater at the time,
   wherein if the information representing the profile received does not include information representing a target value of the parameter related to the operation of the heater in a first time period, the program causing the computer to use information representing a target value of the parameter related to the operation of the heater in a second time period as the information representing the target value of the parameter related to the operation of the heater in the first time period, the second time period being one time period before the first time period.

* * * * *